(12) United States Patent
Koyama

(10) Patent No.: US 9,351,631 B2
(45) Date of Patent: May 31, 2016

(54) BENDING ANGLE ADJUSTMENT MECHANISM FOR ENDOSCOPE AND ENDOSCOPE HAVING THE BENDING ANGLE ADJUSTMENT MECHANISM

(71) Applicant: OLYMPUS CORPORATION, Tokyo (JP)

(72) Inventor: Reiji Koyama, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 77 days.

(21) Appl. No.: 14/445,578

(22) Filed: Jul. 29, 2014

(65) Prior Publication Data

US 2015/0025319 A1    Jan. 22, 2015

Related U.S. Application Data

(63) Continuation of application No. PCT/JP2013/077096, filed on Oct. 4, 2013.

(30) Foreign Application Priority Data

Jan. 11, 2013    (JP) ................. 2013-003844

(51) Int. Cl.
*A61B 1/04*    (2006.01)
*A61B 1/00*    (2006.01)
*A61B 1/008*    (2006.01)
*A61B 1/005*    (2006.01)
*A61B 1/01*    (2006.01)
*A61B 1/313*    (2006.01)

(52) U.S. Cl.
CPC .............. *A61B 1/008* (2013.01); *A61B 1/0011* (2013.01); *A61B 1/0052* (2013.01); *A61B 1/0057* (2013.01); *A61B 1/01* (2013.01); *A61B 1/313* (2013.01)

(58) Field of Classification Search
CPC .... A61B 1/0055; A61B 1/008; A61B 1/0057; A61B 1/0011; A61B 1/0052
USPC .......... 600/104, 108, 114, 139–152; 604/510, 604/95.04, 103.03, 528; 348/45, 65
See application file for complete search history.

(56) References Cited

U.S. PATENT DOCUMENTS

2008/0086031 A1    4/2008    Mitsuya

FOREIGN PATENT DOCUMENTS

JP    61-121801 U    7/1986
(Continued)

OTHER PUBLICATIONS

Machine Translation JP09-238895, 16 pages.*
(Continued)

*Primary Examiner* — Anhtuan T Nguyen
*Assistant Examiner* — Timothy J Neal
(74) *Attorney, Agent, or Firm* — Scully, Scott, Murphy & Presser, P.C.

(57) ABSTRACT

A bending angle adjustment mechanism for an endoscope includes a rod member that is disposed along a traveling path of a long member that is connected to a bending portion that is bendable and is pulled, a support member made of metal that is integrally provided to support both ends of the rod member, an adjustment piece that is engaged with the rod member, is movable along the rod member, and restricts movement of the long member, a guide member made of resin having a guide surface for guiding movement of the adjustment piece, wherein the guide member is fixed in a state in which the guide member is sandwiched between the adjustment piece and the support member so that the guide surface is disposed in a position capable of guiding the adjustment piece.

7 Claims, 18 Drawing Sheets

(56) References Cited

FOREIGN PATENT DOCUMENTS

| | | |
|---|---|---|
| JP | 09-238895 A | 9/1997 |
| JP | 10-276966 A | 10/1998 |
| JP | 2000-051146 A | 2/2000 |
| JP | 2000-051148 A | 2/2000 |
| JP | 2007-054452 A | 3/2007 |

OTHER PUBLICATIONS

Machine Translation JP2000-51146, 32 pages.*
International Search Report dated Nov. 5, 2013 issued in PCT/JP2013/077096.
Extended Supplementary European Search Report dated Feb. 10, 2016 from related European Application No. 13 87 0672.6.

* cited by examiner

BENDING ANGLE ADJUSTMENT MECHANISM FOR ENDOSCOPE AND ENDOSCOPE HAVING THE BENDING ANGLE ADJUSTMENT MECHANISM

CROSS REFERENCE TO RELATED APPLICATION

This application is a continuation application of PCT/JP2013/077096 filed on Oct. 4, 2013 and claims benefit of Japanese Application No. 2013-003844 filed in Japan on Jan. 11, 2013, the entire contents of which are incorporated herein by this reference.

BACKGROUND OF THE INVENTION

1. Field of the Invention

The invention relates to a bending angle adjustment mechanism for an endoscope that is a mechanism for setting a maximum bending angle of the endoscope, and is for adjusting a moving amount, and a moving range of bending operation wires and chains, in a bending operation mechanism for performing a bending operation of a bending portion of the endoscope, and an endoscope having the bending angle adjustment mechanism.

2. Description of the Related Art

A conventional flexible endoscope has been normally configured by an elongated insertion portion, and an operation portion that is connected to a proximal end portion of the insertion portion. The insertion portion is configured by an elongated flexible tube portion having flexibility, a bending portion and a distal end configuring portion being connected in sequence from a proximal end side. At the operation portion, a bending operation knob for performing a bending operation of the bending portion is placed. The bending operation knob is connected to a bending operation mechanism that is placed in an inside of the operation portion. That is, a rotating shaft is integrally attached to the bending operation knob, and a rotating wheel (a sprocket) is integrally formed at the rotating shaft. A long member such as a chain is wound on the rotating wheel, and bending operation wires are further connected to both ends of the long member (chain or the like) via connecting members. The bending operation wire is inserted through and disposed in an inside of the insertion portion, and is provided connectively between the bending operation mechanism and the bending portion. By a configuration as above, when the bending operation knob is rotationally operated normally and reversely, the chain and the operation wires are pulled and driven reciprocally via the bending operation mechanism, and a bending operation of the bending portion is realized.

Further, in the conventional flexible endoscope, setting of a bending angle differs according to each model depending on a use purpose, and therefore, the bending operation mechanism which is provided in the inside of the operation portion of the endoscope is provided with a bending angle adjustment mechanism for restricting a maximum bending angle of the bending portion by adjusting a moving amount and a moving range of the long member for each model.

The bending angle adjustment mechanism is configured by having a stopper member that restricts movement of the bending operation wire and the connecting member, a screw member that performs positional adjustment by moving a position of the stopper member along a moving direction of the operation wire, a support member that is fixed to the fixing portion of the operation portion to support the stopper position adjusting screw member rotatably, and respective component members such as a partition wall that guides movement of the connecting member.

By the configuration as above, the maximum bending angle of the bending portion is restricted by movement of the connecting member being restricted by the stopper member, and the stopper member is moved in the moving direction of the operation wire to be positioned by the screw member, whereby setting of the bending angle of the bending portion is enabled.

Concerning the bending angle adjustment mechanism of this type in the conventional bending operation mechanism for an endoscope, bending angle adjustment mechanisms with various configurations have been conventionally disclosed by, for example, Japanese Patent Application Laid-Open Publication No. 2000-051146, Japanese Patent Application Laid-Open Publication No. 2007-054452, Japanese Patent Application Laid-Open Publication No. 09-238895, Japanese Patent Application Laid-Open Publication No. 2000-051148, Japanese Patent Application Laid-Open Publication No. 10-276966 and the like, and have been variously put into practical use.

SUMMARY OF THE INVENTION

A bending angle adjustment mechanism for an endoscope of one aspect of the present invention includes a rod member that is disposed along a traveling path of a long member that is connected to a bending portion that is bendable and is pulled, a support member made of metal that is integrally provided to support both ends of the rod member, an adjustment piece that is engaged with the rod member, is movable along the rod member, and restricts movement of the long member, a guide member made of resin having a guide surface for guiding movement of the adjustment piece, wherein the guide member is fixed in a state in which the guide member is sandwiched between the adjustment piece and the support member so that the guide surface is disposed in a position capable of guiding the adjustment piece.

Further, an endoscope having a bending angle adjustment mechanism of one aspect of the present invention includes the bending angle adjustment mechanism.

DETAILED DESCRIPTION OF THE PREFERRED EMBODIMENT

Figure 1:
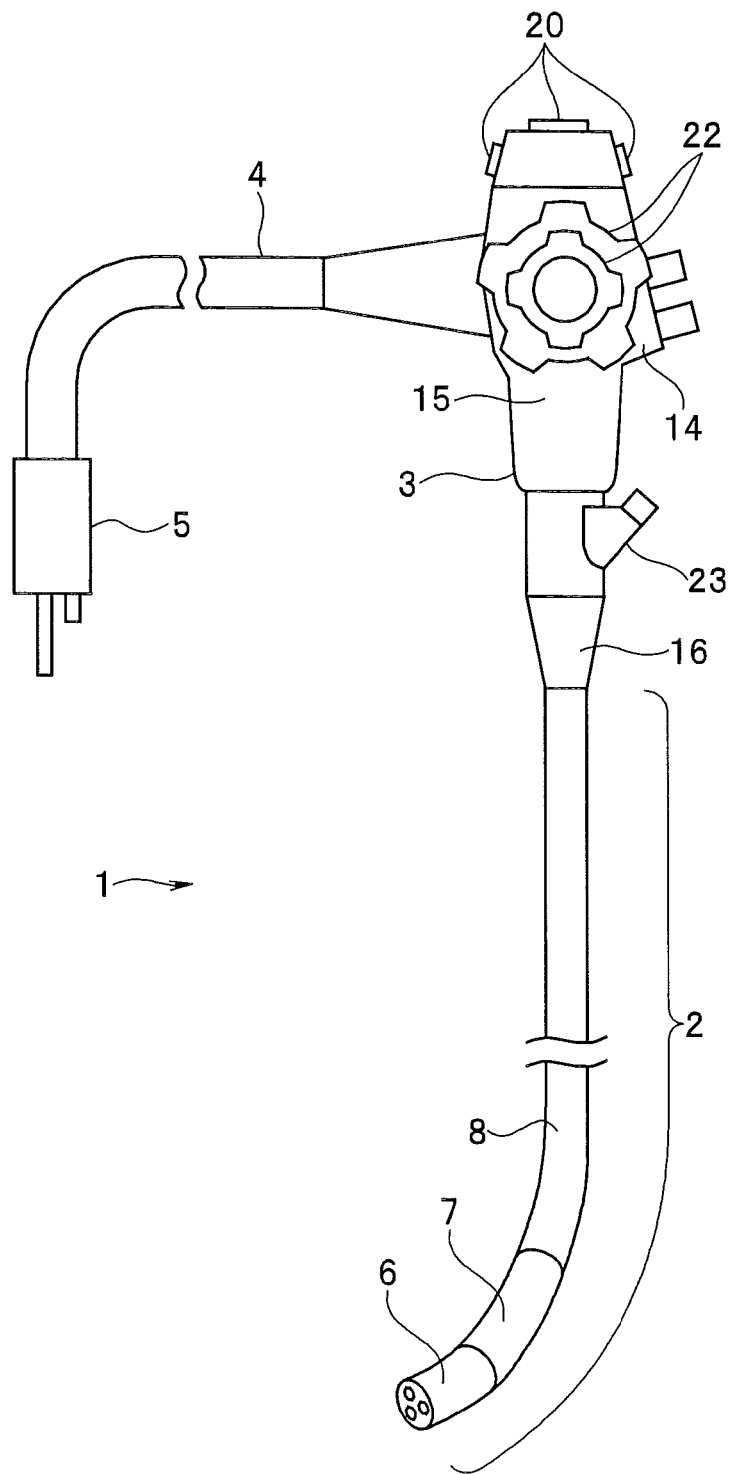
FIG. 1 is a schematic configuration view showing an entire configuration of an endoscope to which a bending angle adjustment mechanism of one embodiment of the present invention is applied.

Hereinafter, the present invention will be described based on an embodiment shown in the drawings.

Note that in the respective drawings for use in the following explanation, respective component elements are sometimes shown with scale made to differ according to the respective component elements in order to make the respective component elements shown in such sizes as to be recognizable on the drawings. Accordingly, the present invention is not limited only to forms illustrated in the drawings, in terms of numbers and quantities of the component elements, shapes of the component elements, ratios of sizes of the component elements and relative positional relations of the respective component elements that are illustrated in the drawings.

First of all, an entire configuration of an endoscope to which a bending angle adjustment mechanism of one embodiment of the present invention is applied, and a schematic configuration of a bending operation mechanism of the endoscope will be briefly described.

Figure 2:
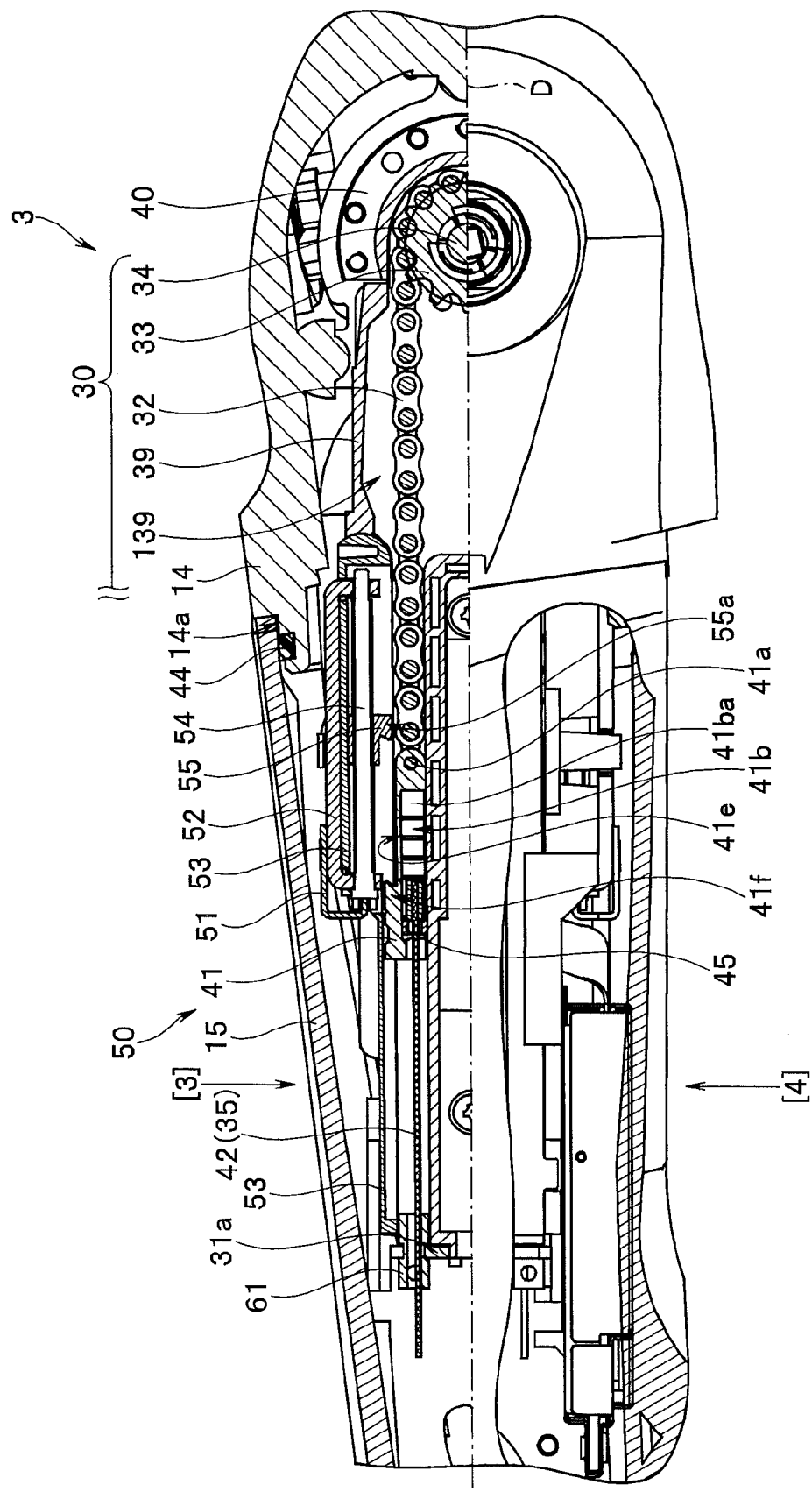
FIG. 2 is an essential part enlarged sectional view showing a part of an internal configuration of an operation portion in the endoscope of FIG. 1.
Figure 3:
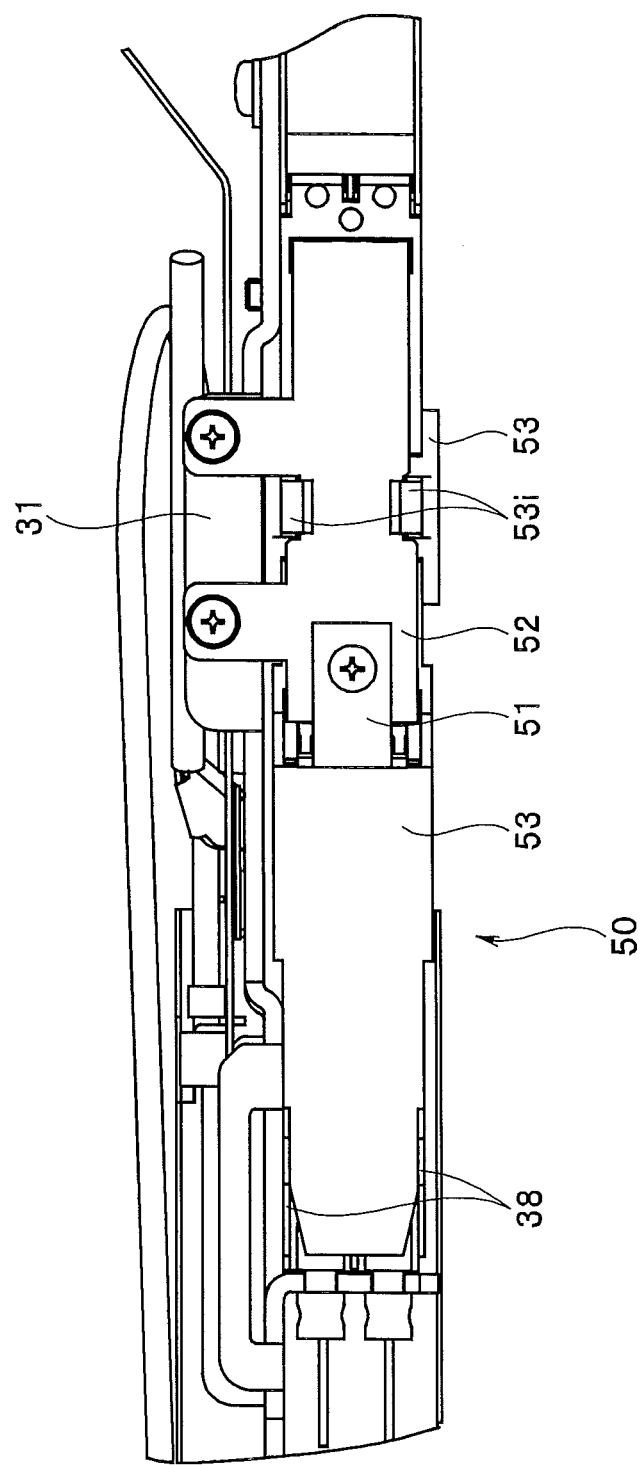
FIG. 3 is an arrow view of the internal configuration in a case seen from a direction of an arrow [3] of FIG. 2.
Figure 4:
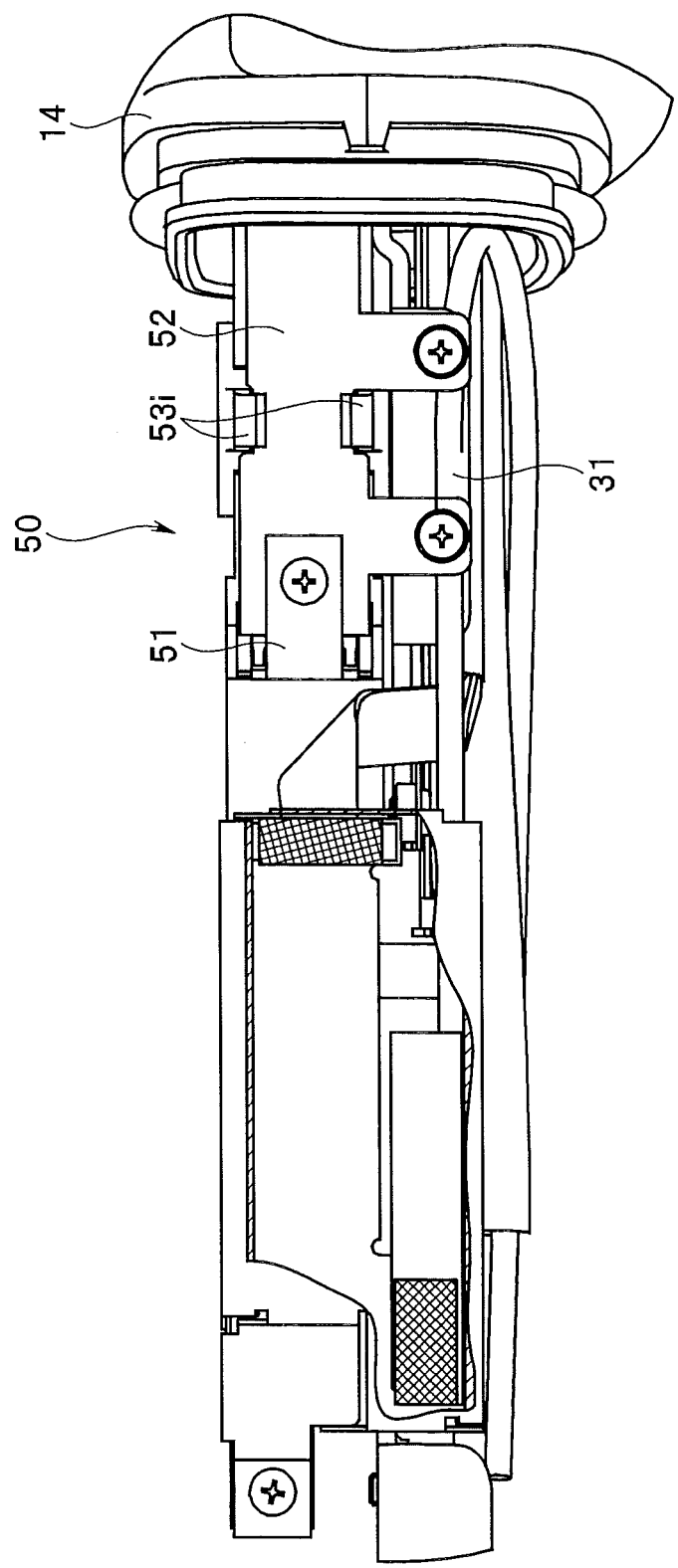
FIG. 4 is an arrow view of the internal configuration in a case seen from a direction of an arrow [4] of FIG. 2.
Figure 5:
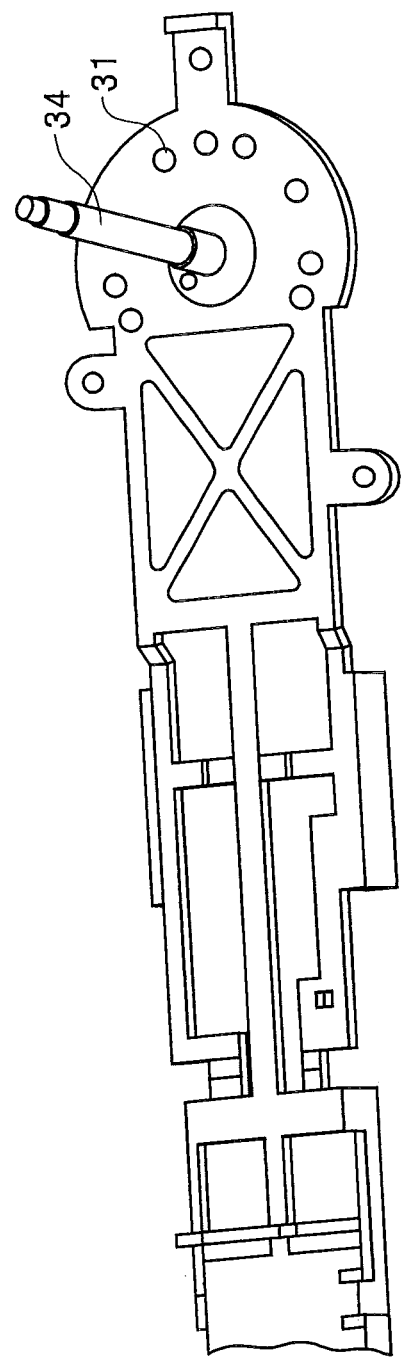
FIG. 5 is an essential part enlarged perspective view showing a part of a main frame of the operation portion of the endoscope of FIG. 1 with the main frame extracted.
Figure 6:
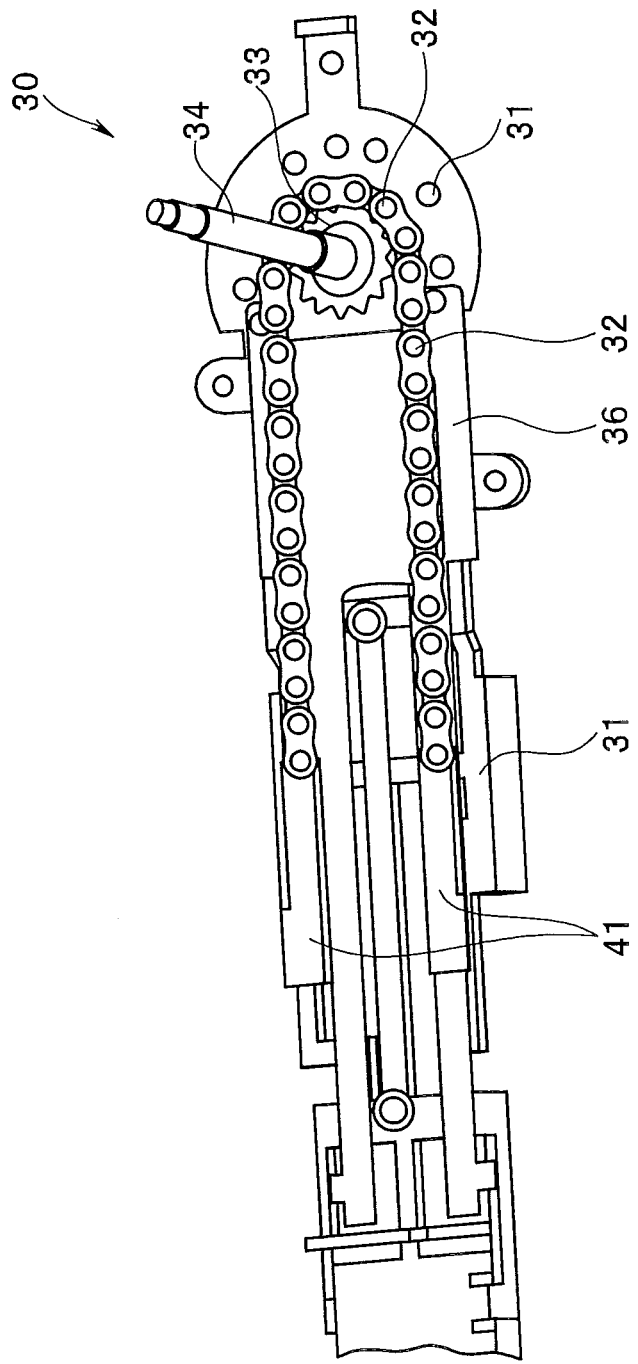
FIG. 6 is an essential part enlarged perspective view showing a state in which some of component members of the bending operation mechanism are attached to the main frame of FIG. 5.
Figure 7:
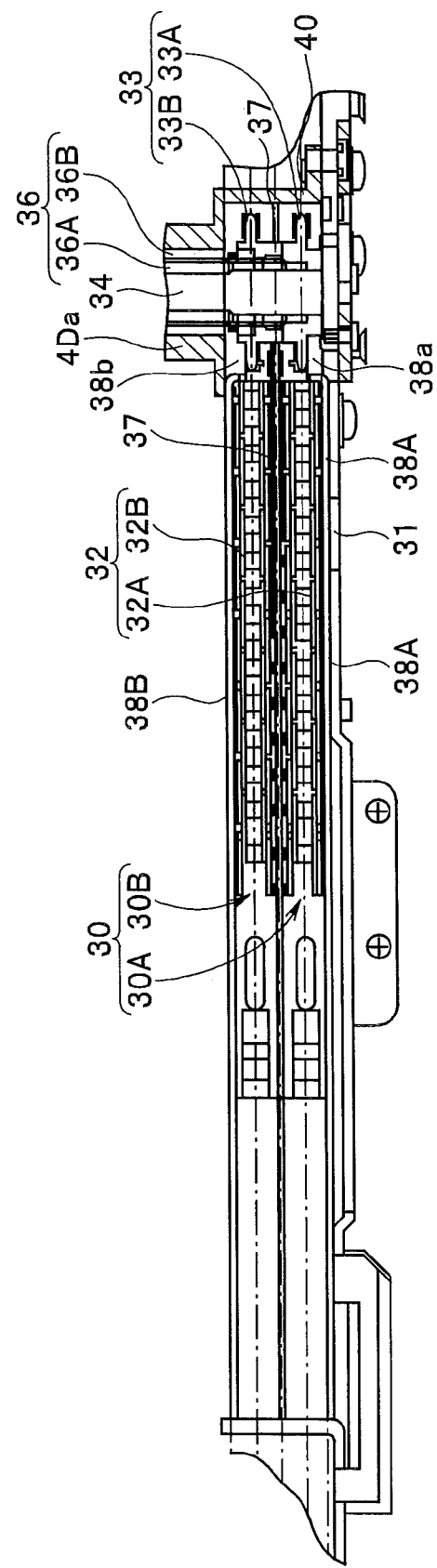
FIG. 7 is an essential part enlarged sectional view showing a part of the bending operation mechanism of the operation portion of the endoscope of FIG. 1.

FIG. 1 is a schematic configuration view showing an entire configuration of an endoscope to which a bending angle adjustment mechanism of one embodiment of the present invention is applied. FIG. 2 is an essential part enlarged sectional view showing a part of an internal configuration of an operation portion in the endoscope of FIG. 1. FIG. 3 is an arrow view of the internal configuration in a case seen from a direction of an arrow [3] of FIG. 2. FIG. 4 is an arrow view of the internal configuration in a case seen from a direction of an arrow [4] of FIG. 2. Note that in FIG. 3 and FIG. 4, in order to illustrate the internal configuration, illustration of exterior components is omitted. FIG. 5 is an essential part enlarged perspective view showing a part of a main frame of the operation portion of the endoscope of FIG. 1 with the main frame extracted. FIG. 6 is an essential part enlarged perspective view showing a state in which some of component members of the bending operation mechanism are attached to the main frame of FIG. 5. FIG. 7 is an essential part enlarged sectional view showing a part of the bending operation mechanism of the operation portion of the endoscope of FIG. 1.

An endoscope 1 to which a bending angle adjustment mechanism 50 of the present embodiment is applied is mainly configured by an elongated insertion portion 2 to be inserted into a body cavity, an operation portion 3 that is provided connectively to a proximal end side of the insertion portion 2, a universal cord 4 a proximal end portion of which is connected to one side surface of the operation portion 3, a connector 5 that is placed at a distal end portion of the universal cord 4, a bending operation mechanism 30 and the bending angle adjustment mechanism 50 included in the bending operation mechanism 30 and the like. Note that the present endoscope 1 is configured to operate as an endoscope system by being connected to a light source apparatus and a control apparatus such as a video processor that are not illustrated via the connector 5.

The insertion portion 2 is configured by a rigid distal end configuring portion 6, a bending portion 7 and a flexible tube portion 8 in an elongated shape having flexibility being connected in sequence from a distal end. Note that the bending portion 7 is configured to be capable of being bent and operated by the bending operation mechanism 30 (a detailed configuration will be described later) in respective four directions of an up and a down directions and a left and a right directions, and a bending operation in an optional direction is enabled by combination of bending operations in the four directions.

An objective lens, an illumination lens, a cleaning nozzle, a treatment instrument channel opening and the like are placed on a distal end face of the distal end configuring portion 6. Further, in an inside of the distal end configuring portion 6, an air feeding conduit, a water feeding conduit and the like that are connected to the above described cleaning nozzle, a light guide fiber or the like that supplies illuminating light to the illumination lens, and the like are placed (not illustrated), besides electric components such as an image pickup device and an electric substrate and the like, a video cable that is extended from the image pickup device, and the like. The video cable and the light guide fiber are provided continuously to the connector 5 by being inserted through the insides of the insertion portion 2, the operation portion 3 and the universal cord 4. Further, the air feeding conduit and the water feeding conduit are provided continuously to the connector 5 via an air/water feeding cylinder provided in the operation portion 3 and the universal cord 4 by being inserted through the insertion portion 2.

Note that detailed explanation and illustration of an outer surface and an internal configuration of the distal end configuring portion 6 will be omitted, on the assumption that the distal end configuring portion 6 similar to that of the conventional endoscope of an ordinary form is included.

The operation portion 3 is formed to be watertight by casing members such as an exterior casing 14 and a grasping portion casing 15. A proximal end portion of the insertion portion 2 is provided continuously from one end portion of the grasping portion casing 15, and at a joint portion thereof, a bend preventing portion 16 formed of an elastic rubber member or the like to prevent the flexible tube portion 8 of the insertion portion 2 from abruptly bending is provided.

On the exterior casing 14 of the operation portion 3, a plurality of bending operation knobs 22 for performing a bending operation for the bending portion 7 of the insertion portion 2 are rotatably placed on a same axis of a support shaft 34 (see FIG. 2, FIG. 5 and FIG. 6) that is a shaft member (a detailed configuration will be described later). The plurality of bending operation knobs 22 are mechanically connected to the bending operation mechanism 30 (see FIG. 2) that is placed in the inside of the operation portion 3, that is, insides of the exterior casing 14 and the grasping portion casing 15.

Further, on an outer surface of the exterior casing 14 of the operation portion 3, various operation members, for example, a plurality of switches 20 for remotely operating peripheral apparatuses such as a video processor are provided. Further, on an outer surface of the grasping portion casing 15, a treatment instrument introduction port 23 for introducing a treatment instrument or the like not illustrated is provided. The treatment instrument introduction port 23 communicates with an internal treatment instrument channel. The treatment instrument channel is inserted through the inside of the insertion portion 2 to a treatment instrument channel opening of the distal end configuring portion 6.

In the inside of the operation portion 3, the bending operation mechanism 30 is placed as shown in FIG. 2. The bending operation mechanism 30 is a mechanism unit that rotates a sprocket 33 that is a rotating wheel attached to the support shaft 34 by an operator rotating the bending operation knob 22 attached to the support shaft 34 which is the rotating shaft provided in the operation portion 3 which is grasped and operated by an operator, and reciprocally moves a chain 32 that is a long member connected to a bending operation wire 35 that is extended from the bending portion 7 at the distal end of the insertion portion 2 and is wound on the sprocket 33 to move the bending portion 7.

The respective component members of the bending operation mechanism 30 are fixed to a main frame 31 that is placed in the inside of the operation portion 3. The main frame 31 is a structure including a ladder structure as shown in FIG. 5, for example, or a plate structure not illustrated, and is formed of a metal member or the like such as die cast made by injection molding of aluminum. The main frame 31 is fixed by being screwed in the insides of the exterior casing 14 and the grasping portion casing 15.

The bending operation mechanism 30 is configured by a left-and-right bending operation mechanism 30A capable of causing the bending portion 7 to perform a bending operation in a left and a right directions, an up-and-down bending operation mechanism 30B capable of causing the bending portion 7 to perform a bending operation in an up and a down directions, and the like. Here, as shown in FIG. 7, on a top surface of the main frame 31, the left-and-right bending operation mechanism 30A is disposed with a lower side chain cover 38A therebetween. Further, on an upper side of the left-and-right bending operation mechanism 30A, the up-and-down bending operation mechanism 30B is disposed with a partition plate 37 therebetween. On a top surface of the up-and-down bending operation mechanism 30B, an upper side chain cover 38B is disposed. Note that the left-and-right bending operation mechanism 30A and the up-and-down bending operation mechanism 30B are formed of substantially similar configurations.

Respective configuration units of the bending operation mechanism 30 (30A, 30B) are configured by including the bending angle adjustment mechanism 50 and the like besides the component members such as the chain 32 (32A, 32B), the sprocket 33 (33A, 33B), the support shaft 34, a cylindrical body 36 (36A, 36B), the bending operation wire 35, the cylindrical body 36 (36A, 36B), the partition plate 37, and the chain cover 38 (38A, 38B).

The support shaft 34 has a lower end thereof provided by being implanted in the main frame 31 (see FIG. 5 and FIG. 6), while an upper end of the support shaft 34 penetrates through the partition plate 37 and the upper side chain cover 38B, and protrudes to an outside of the exterior casing 14.

The chain cover 38 is formed with use of a thin plate-shaped member made of metal or resin, for example, and as shown in FIG. 7, two of the chain covers 38 are respectively disposed at predetermined sites in such a manner as to cover top and bottom surfaces of the two chains 32A and 32B in a position corresponding to a travel portion of the chain 32. Note that a thin plate-shaped member is used as the chain cover 38, and thereby, reduction in weight is realized.

On an outer circumferential face of the support shaft 34, the left-and-right cylindrical body 36A is rotatably disposed, and on an outer circumferential face of the left-and-right cylindrical body 36A, the up-and-down cylindrical body 36B is rotatably disposed. In the above case, the left-and-right cylindrical body 36A and the up-and-down cylindrical body 36B are respectively rotatable independently. At an upper end of the left-and-right cylindrical body 36A, a left-and-right bending operation knob 22A is fixedly provided, and at an upper end of the up-and-down cylindrical body 36B, an up-and-down bending operation knob 22B is fixedly provided. Further, at the lower end of the support shaft 34, the two sprockets 33 are respectively placed rotatably, that is, a left-and-right sprocket 33A of the left-and-right bending operation mechanism 30A is placed at a lower side, whereas an up-and-down sprocket 33B of the up-and-down bending operation mechanism 30B is placed at an upper side. In the above case, the left-and-right sprocket 33A is fixedly provided at a lower end of the left-and-right cylindrical body 36A at an inner side. Further, the up-and-down sprocket 33B is fixedly provided at a lower end of the up-and-down cylindrical body 36B at an outer side (see FIG. 7: FIG. 6 shows only one sprocket as reference sign 33). That is, a plurality of sprockets 33 (rotating wheels) are provided along a longitudinal direction of the support shaft 34 (rotating shaft), and the respective chains 32 (long members) connected to the bending operation wire 35 are respectively wound on the respective sprockets 33 (rotating wheels). By the configuration, the left-and-right sprocket 33A is connected to the left-and-right bending operation knob 22A via the left-and-right cylindrical body 36A, and the up-and-down sprocket 33B is connected to the up-and-down bending operation knob 22B via the up-and-down cylindrical body 36B.

The left-and-right chain 32A is meshed with the left-and-right sprocket 33A, and the up-and-down chain 32B is meshed with the up-and-down sprocket 33B, respectively. Here, presser portions (38a, 38b: see FIG. 7) are provided to prevent the respective sprockets 33A and 33B from moving in the axial direction of the support shaft 34 to restrict the respective sprockets 33A and 33B to be positioned in predetermined positions on the support shaft 34, and to prevent the respective chains 32A and 32B from being rolled into the respective sprockets 33A and 33B.

The presser portions (38a, 38b) are sites that are each integrally formed in a form in which a predetermined site of the chain cover 38 is folded. That is, the first presser portion 38a is formed in a site that is a predetermined site of the lower side chain cover 38A facing an undersurface side of the left-and-right sprocket 33A, and is near to the insertion portion 2 with respect to the support shaft 34. Further, the second presser portion 38b is formed in a site that is a predetermined site of the upper side chain cover 38B facing a top surface side of the up-and-down sprocket 33B, and is near to the insertion portion 2 with respect to the support shaft 34.

Further, as shown in FIG. 2, in order to form a space portion 139 for preventing the two chains 32 from running out sideway, and absorbing slackness of the two chains 32 that occurs at a time of a bending operation, a side wall site 39 is formed at a side edge portion of the partition plate 37. The side wall site 39 is formed integrally with the partition plate 37 by resin outset molding or the like.

Further, as shown in FIG. 2 and FIG. 7, on the outer circumferential portions of the two sprockets 33, a cover member 40 that prevents the two chains 32 from being detached is fixed to the main frame 31 by being screwed thereto. A cylinder portion 40a (not illustrated in FIG. 2. only illustrated in FIG. 7) in which the two cylindrical bodies 36 are inserted is fixed to the cover member 40 by being screwed thereto.

Connecting members 41 are fixedly provided at end portions of the respective chains 32a, 32B. A proximal end portion of the bending operation wire 35 that is inserted through the insertion portion 2 is connectively provided at the connecting member 41. A distal end portion of the bending operation wire 35 is fixed to a distal end site (not illustrated) of the bending portion 7 of the insertion portion 2. The bending operation wire 35 is produced by a plurality of wires being twisted, and stranded wires having flexibility are used.

The bending operation wire 35 is inserted through a coil pipe 61 (see FIG. 2) in a vicinity of a distal end portion of a guide block 53 (described later) of the bending angle adjustment mechanism 50 (a detailed configuration will be described later), and thereafter, is extended to a side of the insertion portion 2. The coil pipe 61 is formed of a tubular member having an inside diameter set to be slightly larger than a diameter of the bending operation wire 35, and is fitted in and fixed to a coil pipe fixing portion 31a that is provided at the main frame 31. The coil pipe fixing portion 31a is a site that is formed integrally with the main frame 31, and is a site configured to be able to elastically grasp an outside diameter portion of the coil pipe 61. The coil pipe 61 is a component member that has a function of preventing disturbance of the bending operation wire 35 which is slackened by a bending operation.

By the configuration as above, when the left-and-right bending operation knob 22A is rotationally operated, the rotation is transmitted to the left-and-right sprocket 33A via the left-and-right cylindrical body 36A, and the left-and-right sprocket 33A rotates in a same direction together with the left-and-right bending operation knob 22A. Subsequently, when the left-and-right sprocket 33A rotates, the left-and-right chain 32A is driven to travel with the rotation, and the bending operation wire 35 which is connected thereto via the connecting member 41 is pulled and driven with traveling of the left-and-right chain 32A, whereby the bending portion 7 is operated to bend in either the left or the right direction.

Similarly to the above, when the up-and-down bending operation knob 22B is rotationally operated, the rotation is transmitted to the up-and-down sprocket 33B via the up-and-down cylindrical body 36B, and the up-and-down sprocket 33B rotates with the up-and-down bending operation knob 22B. Subsequently, when the up-and-down sprocket 33B rotates, the up-and-down chain 32B is driven to travel with the rotation, and with traveling of the up-and-down chain 32B, the bending operation wire 35 which is connected thereto via the connecting member 41 is pulled and driven, whereby the bending portion 7 is operated to bend in either the up or the down direction.

Note that in a distal end site of the exterior casing 14, a ring-shaped fitting concave portion 14a that is fitted to a rear end portion of the grasping portion casing 15 is formed. The rear end portion of the grasping portion casing 15 is attached by being fitted to the fitting concave portion 14a of the exterior casing 14, and is connected in a state in which an end face and an inner face thereof abut on the fitting concave portion 14a of the exterior casing 14. Here, in an abutment portion of the rear end portion of the grasping portion casing 15 and the fitting concave portion 14a of the exterior casing 14, an O-shaped ring 44 is fitted. The O-shaped ring 44 is means that watertightly seals the abutment site of the exterior casing 14 and the grasping portion casing 15.

A connecting portion of the connecting member 41 and the bending operation wire 35 is configured as follows. That is, as shown in FIG. 2 (see also FIG. 1), a connecting portion 41a that is connected to a terminal end of the chain 32 is formed at a rear end portion of the connecting member 41.

Figure 11:
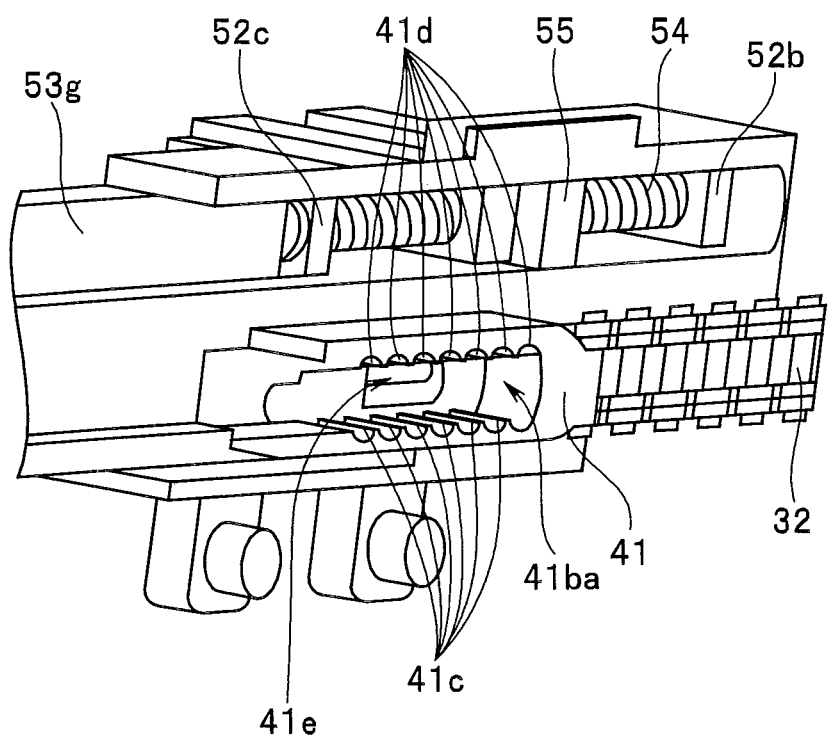
FIG. 11 is an essential part enlarged view showing a part of FIG. 9 under enlargement, and is a view mainly showing a connection structure of a chain and a connecting member.

Further, the connecting member 41 is provided with a wire locking portion 41b that detachably locks the proximal end portion of the bending operation wire 35. In the wire locking portion 41b, an engaging space 41ba having an opening in one side face of the connecting member 41 is formed. In the engaging space 41ba, a plurality of engaging convex portions 41c (FIG. 11) that are provided to protrude toward an inner side are provided side by side along an axial direction of the bending operation wire 35. Here, as shown in FIG. 11, in the engaging space 41ba, a plurality of circular grooves 41d are provided connectively along the axial direction of the bending operation wire 35, whereby the engaging convex portions 41c are formed by connectively provided portions among the adjacent circular grooves 41d.

Further, on the other side surface (a bottom face of the engaging space 41ba) of the connecting member 41, a long hole 41e that is provided extensively along the axial direction of the bending operation wire 35, and a convex portion 41f that protrudes toward an outside that is in a direction orthogonal to the axial direction of the connecting member 41, protrudes toward a proximal end side, and is formed into a substantially claw shape are formed. Here, the long hole 41e is formed in a site near to the connecting portion 41a to the chain 32, and is set to have a width narrower than a width of the engaging space 41ba. Further, the convex portion 41f is formed at a side of the connecting portion to the bending operation wire 35 from the long hole 41e. Note that the convex portion 41f abuts on and engages with a concave portion 55a of a stopper 55 that will be described later, and thereby movement of the connecting member 41 in the axial direction of the bending operation wire 35 is configured to be restricted (details will be described later).

A locking member 45 formed into a drum shape is fixedly provided at the proximal end portion of the bending operation wire 35 with use of fixing means such as soldering, brazing, or crimping. When the locking member 45 is inserted in any one of the plurality of circular grooves 41d, the locking member 45 engages with corresponding one of the plurality of engaging convex portions 41c. By being brought into the state, the locking member 45 is engaged and fixed in the engaging space 41ba. In this manner, the bending operation wire 35 is connected to the chain 32 via the connecting member 41. In this case, adjustment of a fixing position of the bending operation wire 35 in the axial direction can be performed depending on which of the plurality of circular grooves 41d the locking member 45 is inserted in. Note that as shown in FIG. 2, movement in the axial direction of the connecting member 41 is guided by the guide block 53 of the bending angle adjustment mechanism 50 and a guide wall 31b that is formed at the main frame 31.

Figure 8:
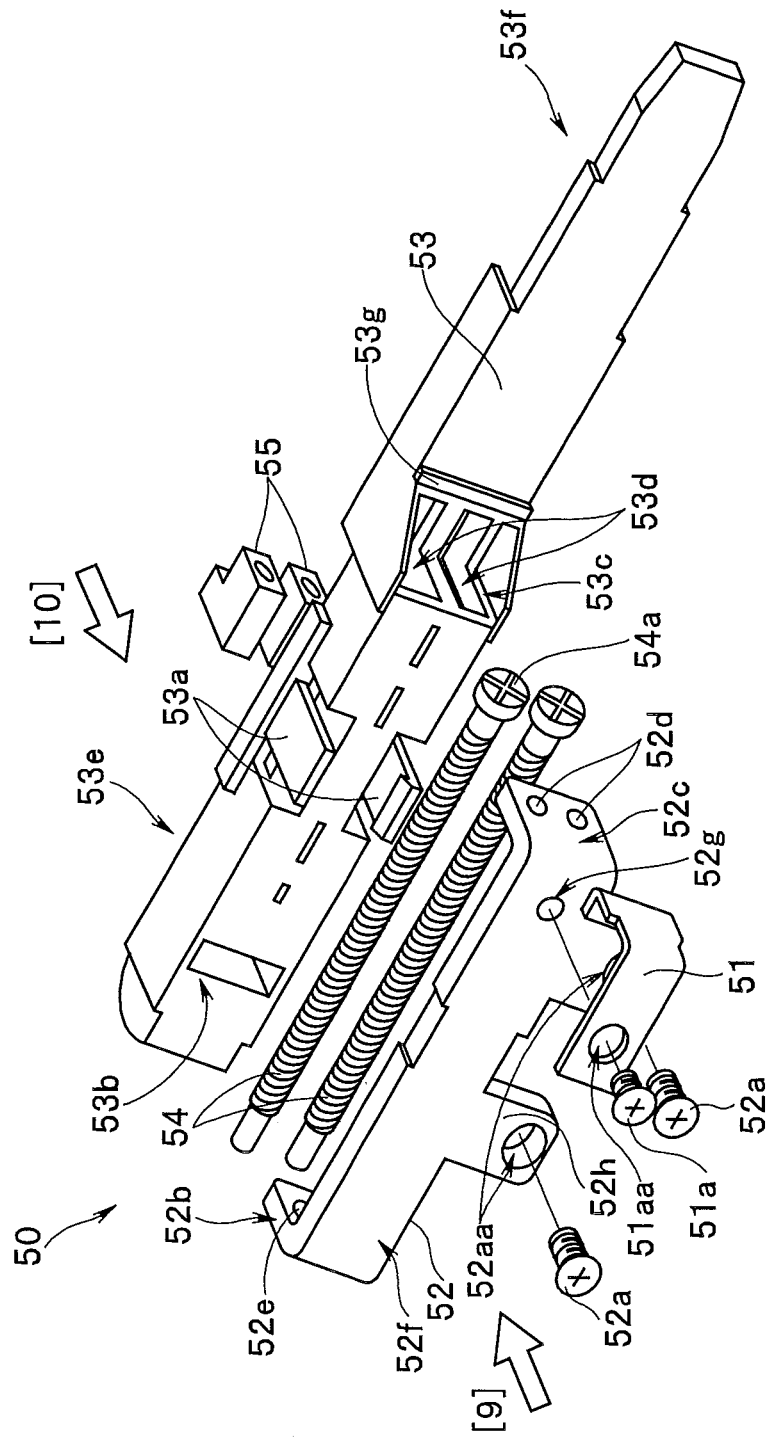
FIG. 8 is an essential part enlarged exploded perspective view showing main component members of the bending angle adjustment mechanism of one embodiment of the present invention with the main component members extracted.
Figure 9:
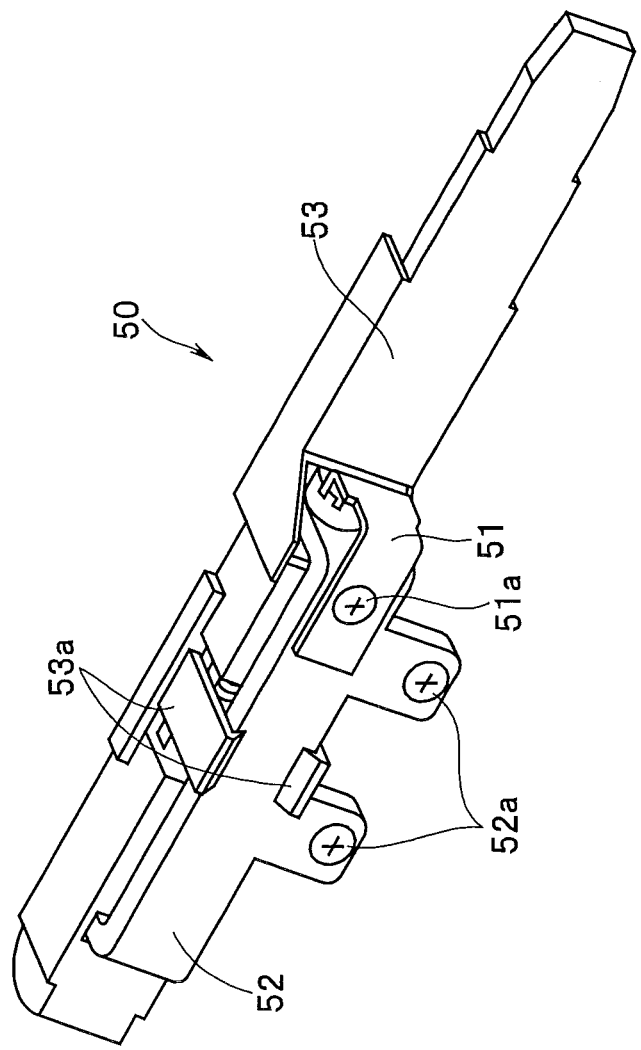
FIG. 9 is an essential part enlarged assembled perspective view showing a state in which the bending angle adjustment mechanism of FIG. 8 is assembled, and is a view showing a state seen from a direction of an arrow [9] of FIG. 8.
Figure 10:
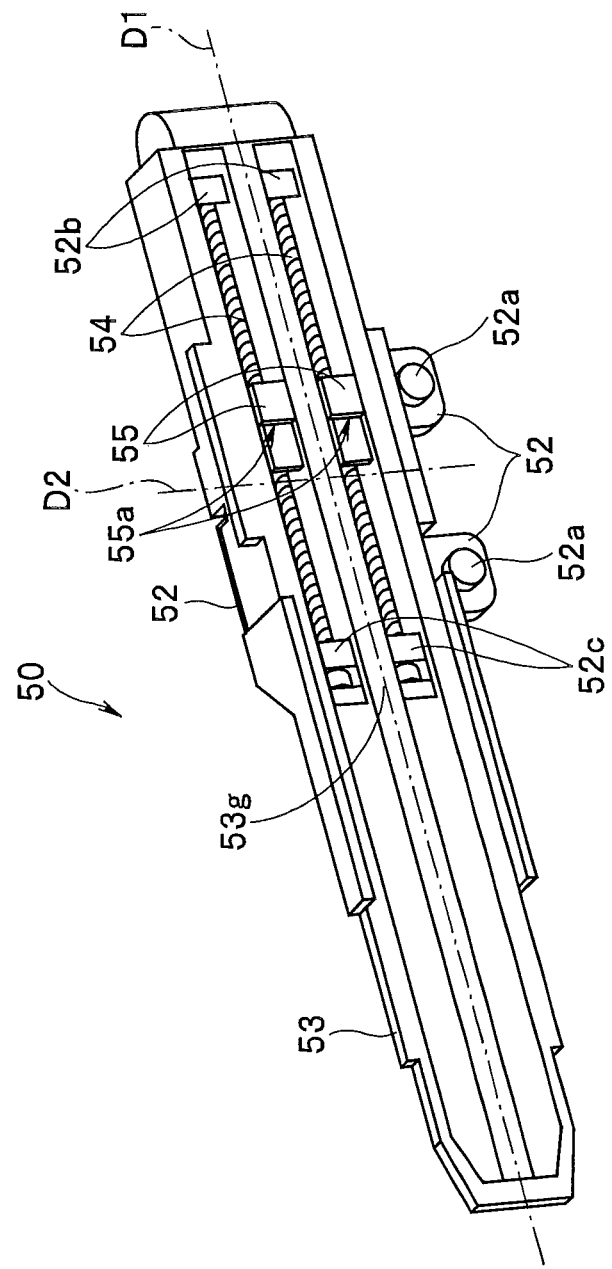
FIG. 10 is an essential part enlarged assembled perspective view showing a state in which the bending angle adjustment mechanism of FIG. 8 is assembled, and is a view showing a state seen from a direction of an arrow [10] of FIG. 8.
Figure 12:
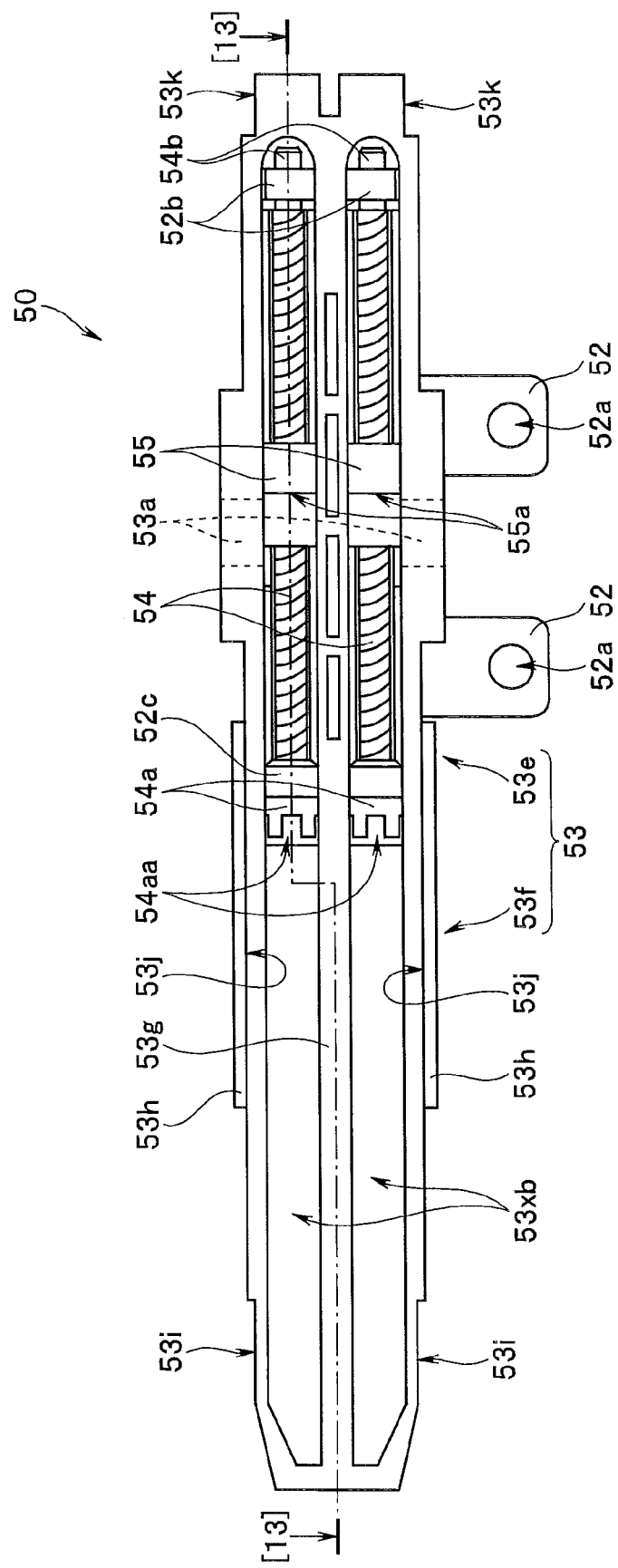
FIG. 12 is a plan view on a side shown in FIG. 10, in the bending angle adjustment mechanism of FIG. 8.
Figure 13:
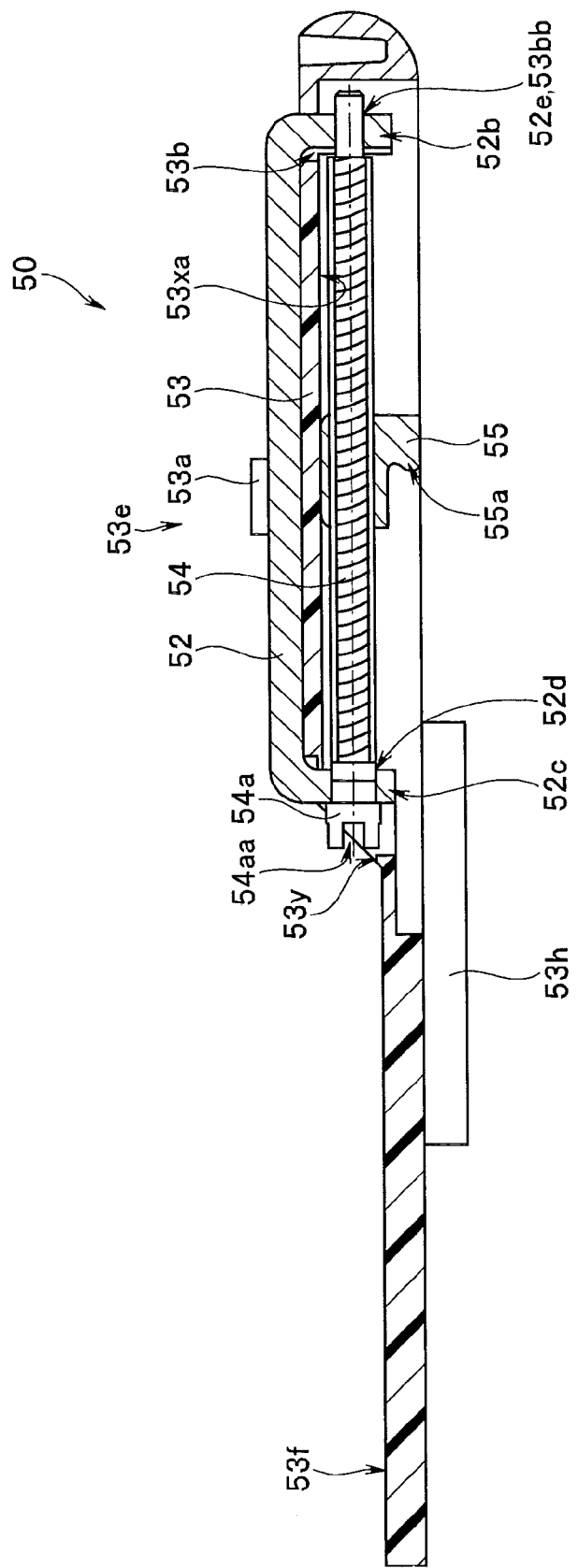
FIG. 13 is a sectional view taken along a line [13]-[13] of FIG. 12.
Figure 14:
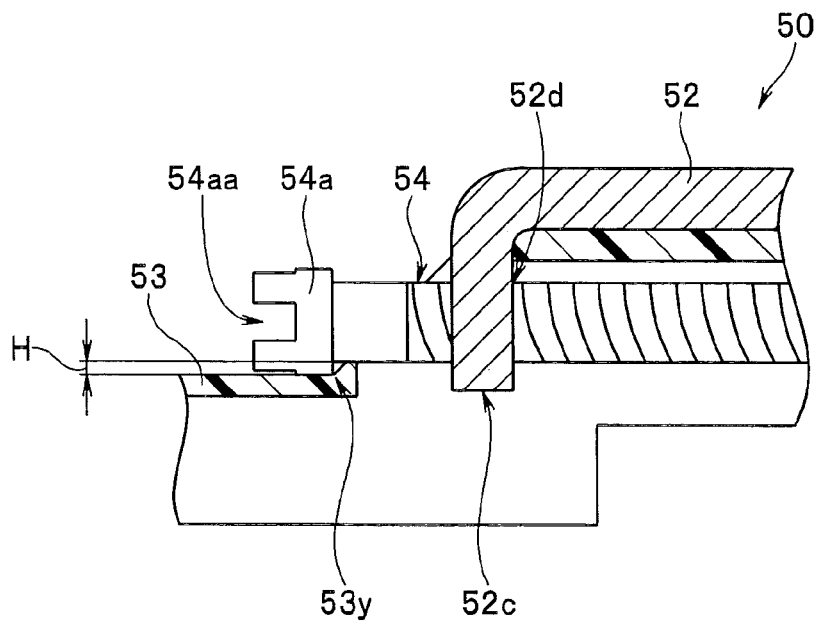
FIG. 14 is an essential part enlarged sectional view showing a part of FIG. 13 under enlargement, and is a view showing a state in a middle of insertion of an adjustment shaft into a guide block.
Figure 15:
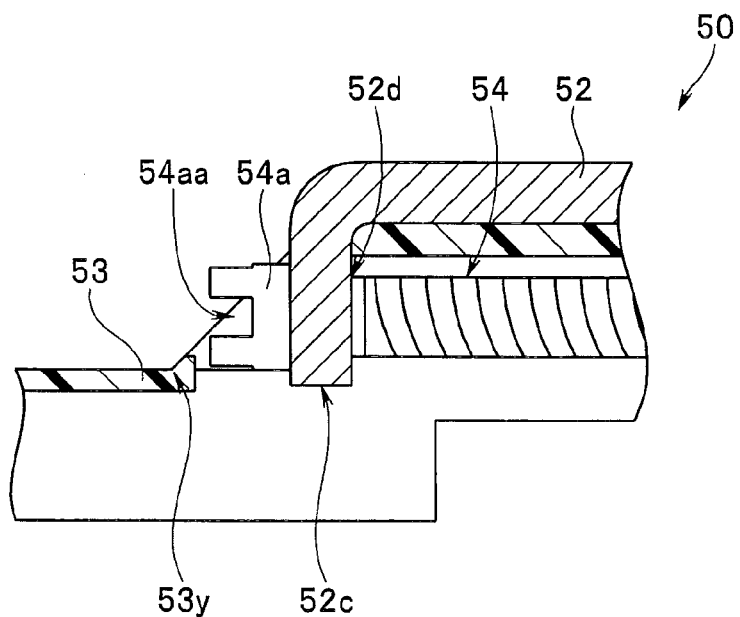
FIG. 15 is an essential part enlarged sectional view showing a part of FIG. 13 under enlargement, and is a view showing a state in which the adjustment shaft is attached to a predetermined position of the guide block.

Next, a detailed configuration of the bending angle adjustment mechanism 50 will be described hereinafter with use of FIG. 8 to FIG. 15. FIG. 8 is an essential part enlarged exploded perspective view showing main component members of the bending angle adjustment mechanism of the present embodiment with the main component members extracted. FIG. 9 and FIG. 10 are essential part enlarged assembled perspective views each showing a state in which the bending angle adjustment mechanism of FIG. 8 is assembled. Of FIG. 9 and FIG. 10, FIG. 9 is a view showing a state seen from a direction of an arrow [9] of FIG. 8. FIG. 10 is a view showing a state seen from a direction of an arrow [10] of FIG. 8. FIG. 11 is an essential part enlarged view showing a part of FIG. 9 under enlargement, and is a view mainly showing a connection structure of a chain and a connecting member. FIG. 12 is a plan view of a side shown in FIG. 10, in the bending angle adjustment mechanism of the present embodiment. FIG. 13 is a sectional view taken along a line [13]-[13] of FIG. 12. FIG. 14 and FIG. 15 are essential part enlarged sectional views each showing a part of FIG. 13 under enlargement. Of FIG. 14 and FIG. 15, FIG. 14 is a view showing a state in a middle of insertion of an adjustment shaft into a guide block. FIG. 15 shows a state in which the adjustment shaft is attached to a predetermined position of a guide block.

The bending angle adjustment mechanism 50 of the present embodiment is a mechanism unit that is provided in the inside of the operation portion 3, and is for setting respective maximum bending angles to the four directions that are the up and the down directions and the left and the right directions of the bending portion 7, as shown in FIG. 2. The bending angle adjustment mechanism 50 is fixed to the main frame 31 by being screwed thereto, for example.

As for the detailed configuration of the bending angle adjustment mechanism 50, the bending angle adjustment mechanism 50 is configured mainly by a screwing member 51, a bearing plate 52, a guide block 53, two adjustment shafts 54, two stoppers 55 and the like, as shown in FIG. 8 to FIG. 13.

The guide block 53 is a guide member that has a portion that is sandwiched and fixed by the adjustment shafts 54 (rod members) and the bearing plate 52 (described later; a plate member), is disposed to be parallel to the adjustment shafts 54 (rod members) and the bearing plate 52 (plate member), and is provided with a guide surface (described later), which is a guide path that guides positions of the stoppers 55 (adjustment pieces) and is a guide surface, in the axial direction (longitudinal direction) of the insertion portion 2.

The guide block 53 is formed by having a first guide portion 53e and a second guide portion 53f. The first guide portion 53e is a site that includes a space in which the two adjustment shafts 54 are placed, guides movement in the axial direction of the two stoppers 55 which are disposed by being screwed onto the respective adjustment shafts 54, and restricts rotation of the respective stoppers 55 around the shafts. Further, the second guide portion 53f is a site that guides movement of the two connecting members 41 in the axial direction, and restricts rotation around an axis and sideway displacement of the respective connecting members 41. Here, the adjustment shaft 54 is a rod member which is provided to extend in the axial direction (longitudinal direction) of the insertion portion 2, and has a threaded portion formed on a surface in a longitudinal direction. Further, the stopper 55 is an adjustment piece that is screwed onto the threaded portion (a spiral groove that will be described later) of the adjustment shaft 54 (rod member), and is positioned in the threaded portion of the adjustment shaft 54.

When more detailed explanation is made, the first guide portion 53e is formed into a substantially box shape that forms three surfaces with wall surfaces to cover outer edges of the spiral grooves which are screw groove portions of the two adjustment shafts 54, and has an opening in one surface. In the opening site, two groove portions 53x that will be described later are formed. The second guide portion 53f is formed into a substantially plate shape, a part thereof is formed into a substantially box shape having a wall surface (see reference sign 53h that will be described later), and in the one surface, groove portions in which the above described two groove portions 53x extend in a continuing form are formed. Here, the wall surface with three faces that cover the spiral groove of the adjustment shaft 54 in the first guide portion 53e functions as the guide surface that is a guide surface that guides movement of the stopper 55 in the axial direction. In this case, a bottom surface of the first guide portion 53e is specially set as a guide surface 53xa (see FIG. 13). Further, in the second guide portion 53f, the two groove portions 53x are travel surfaces for the chain 32 and the connecting member 41, and are guide surfaces 53xb (see FIG. 12) that are guide surfaces for the connecting member 41 and the chain 32. That is, in the guide block 53 (guide member), the guide surfaces 53xa and 53xb (guide paths) that are a plurality of guide surfaces where the respective chains 32 (long members) respectively pass are integrally provided.

A wall portion 53h (see FIG. 12) is formed to cover part of both side edge portions of the two groove portions 53x which will be described later are formed in a site that is a site in a middle of the guide block 53 and is laid on the first guide portion 53e and the second guide portion 53f. The wall portion 53h is provided to protrude toward a surface side on which the above described two groove portions 53x are formed, which is a direction orthogonal to the axial direction of the guide block 53.

Further, at both side edge portions of a site in a middle of the first guide portion 53e, a snap fit portion 53a that protrudes in a direction opposite to the protruding direction of the above described wall portion 53h is provided to protrude. The snap fit portion 53a is a site that functions as fixing means that is provided to elastically coupling and integrating the guide block 53 and the bearing plate 52 (described later). Thereby, a function of restricting the stoppers 55 from moving in the orthogonal direction to the guide surfaces (the two groove portions 53x) of the guide block 53 is performed. That is, the guide block 53 is integrated with the bearing plate 52 fixed to the main frame 31 by being screwed thereto, by the snap fit portion 53a. Thereupon, the stoppers 55 which are integrally placed at the bearing plate 52 via the adjustment shafts 54 are restricted from moving in the orthogonal direction to the guide surfaces (the two groove portions 53x) of the guide block 53. Here, the bearing plate 52 is a plate member that is provided to be parallel to the axial direction (longitudinal direction) of the adjustment shaft 54 (rod member), has both ends formed by being curved in a substantially perpendicular direction, and has the adjustment shafts 54 (rod members) inserted through and rotatably supported pivotally in the both ends. Note that the guide block 53 is formed by integral molding using a raw material having elasticity, for example, a resin raw material such as polyacetal or the like. In the guide block 53, the two grooves 53x are formed from a proximal end side to a distal end side, as described above. The two groove portions 53x are provided to place the two chains 32 and the two connecting members 41 that are provided connectively to the respective chains 32, and guide movement of the chains 32 and the connecting members 41 according to a bending operation by the bending operation knob 22.

That is, in the first guide portion 53e, the respective two adjustment shafts 54 are placed to be independent and parallel to each other. To this end, in the first guide portion 53e, the two adjustment shafts 54 are placed, and the two groove portions 53x for guiding movement of the two stoppers 55 in the axial direction are formed. The two groove portions 53x are formed to be continuously provided as the groove portions for guiding movement of the two connecting members 41 in the axial direction, in the second guide portion 53f. That is, the two groove portions 53x are integrally formed continuously from the proximal end side of the first guide portion 53e to the distal end side of the second guide portion 53f.

In the first guide portion 53e, a wall surface 53c that positions and fixes a folded portion 52c at one end side of the bearing plate 52 is formed in a middle site, and a concave portion 53b into which a folded portion 52b at the other end side of the bearing plate 52 is fitted and fixed is formed in a site near to the proximal end. In the concave portion 53b, a through-hole 53bb that opens to the axial direction and allows the other end of the adjustment shaft 54 to be inserted therethrough is provided by being bored. The through-hole 53bb is formed in a position axially corresponding to a through-hole 52e of the other end side folded portion 52b of the bearing plate 52. Further, in the wall surface 53c, through-holes 53d that open to the axial direction and allow the adjustment shafts 54 to be inserted therethrough are similarly provided by being bored. The through-holes 53d are formed in positions axially corresponding to through-holes 52d of the one end side folded portion 52c of the bearing plate 52.

When the two adjustment shafts 54 are brought into a state placed at the predetermined sites in the inside of the guide block 53, the two adjustment shafts 54 are placed substantially parallel to each other. In this state, in a site sandwiched between the two adjustment shafts 54, a wall portion 53g that is upright in an orthogonal direction from the guide surfaces 53xa and 53xb are provided extensively in the axial direction. As described above, in the first guide portion 53e of the guide block 53, the space in which the two adjustment shafts 54 are placed is included, and a spiral groove (threaded portion) is provided throughout a substantially total length of a region that is located between the portions that are both ends of the bearing plate 52 (plate member) being folded and facing each other (between the one end side folded portion 52c and the other end side folded portion 52b) when the respective adjustment shafts 54 are disposed in the predetermined sites. Thereby, the spiral groove of the adjustment shaft 54 is configured so that substantially all of the region is protected from the outside, and therefore, there is no fear that the spiral grooves of the adjustment shafts 54 suffer damage or the like. Further, the stoppers 55 have movement in the axial direction guided by the three surfaces, and therefore, can ensure smooth movement without play.

As above, the guide block 53 has an integral structure for simultaneously guiding traveling of the two chains 32. In this case, the guide surfaces 53xa and 53xb that guide movement of the two stoppers 55 and the two connecting members 41 in the axial direction are in the shapes obtained by use of the wall surfaces forming the guide block 53.

The chain cover 38 is placed along both the side edges of the guide block 53. In this case, the two chain covers 38A and 38B are placed in such a manner as to sandwich both the side edge portions 53i shown in FIG. 12, in a distal end side of the guide block 53. In a site in the middle of the guide block 53, the two chain covers 38A and 38B are placed along respective inner walls 53j of the wall portion 53g that are formed at both the side edges. In the proximal end side of the guide block 53, the two chain covers 38A and 38B are placed to sandwich both side edge portions 53k shown in FIG. 12. In this manner, the chain cover 38 is provided in vicinities of the plurality of guide surfaces 53xa and 53xb (guide paths) in the guide block 53 (guide member), and functions as a restricting member that restricts the chain 32 (long member) from moving in the other directions than the axial direction (longitudinal direction) of the same chain 32 (long member).

According to the disposition configuration as above, the chain cover 38 that is disposed in the vicinity of the peripheral portion of the guide block 53 is disposed in a proper position by being positioned and restricted so as not to sag to an inner side in the site in the vicinity of the distal end portion and in the site in the vicinity of the proximal end portion of the guide block 53 and not to sag toward the outer side in the intermediate site, and not to displace in the respective sites.

The bearing plate 52 is a support member that rotatably and pivotally supports respective both end portions of the two adjustment shafts 54. The bearing plate 52 is formed by folding of a metallic plate member or the like, or cutting or the like of a metal block or the like. That is, in the bearing plate 52, an entire body is formed by having a section in a channel shape (a U-shape, a C-shape), the two through-holes 52e that rotatably support respective one ends of the two adjustment shafts 54 are provided by being bored in the folded portion 52b at the other end side, and the two through-holes 52d that rotatably support vicinities of the respective other ends of the two adjustment shafts 54 are provided by being bored in the folded portion 52c at the one end side. Further, at one side edge portion of a flat plate portion 52f of the bearing plate 52, two projectingly provided portions 52h that project outward in a parallel direction with the flat plate portion 52f of the bearing plate 52 are formed. In the respective two projectingly provided portions 52h, through-holes 52aa for inserting screws 52a on an occasion of the bearing plate 52 being screwed and fixed to a predetermined fixing site of the main frame 31 are formed. Further, in the flat plate portion 52f of the bearing plate 52, a screw hole 52g for inserting the screw 51a for fixing and holding the screwing member 51 at a site near to the distal end is provided by being bored. Here, the screwing member 51 is a rotation preventing member that prevents the adjustment shafts 54 (rod members) from rotating with an axial direction (longitudinal direction) as an axis with respect to the guide block 53 (guide member).

As above, the two through-holes 52aa and the screw hole 52g for screw insertion that are formed in the bearing plate 52 are all formed on the same surface. By the configuration, insertion directions of the three screws (51a, 52a) are all in the same direction. The configuration is a contrivance to contribute to improvement in assemblability. Further, the bearing plate 52 is formed to have the section in a channel shape (a U-shape, a C-shape) as a whole as described above. As a result that the shape like this is adopted, both the ends of the adjustment shafts 54 can be supported by one member, and a contribution can be made to improvement in positional precision, such as parallelism to the axial direction of the adjustment shaft 54.

The adjustment shaft 54 is a shaft-shaped member for adjusting the respective maximum bending angles of the four directions that are the up and the down directions and the left and the right directions by adjusting the position of the stopper 55. Therefore, the adjustment shaft 54 has a screw groove portion including a spiral groove formed throughout the substantially total circumference of the shaft portion outer circumferential face, and is configured by having a head portion 54*a* in which an adjusting cross groove 54*aa* (see FIG. 13 and the like) for rotating the shaft portion is formed at one end portion at the distal end side. The adjustment shaft 54 is mounted in a state in which a neck portion of the head portion 54*a* is rotatably supported pivotally in the through-hole 52*d* of the one end side folded portion 52*c* of the bearing plate 52, and the other end portion is rotatably supported pivotally in the through-hole 52*e* of the other end side folded portion 52*b* of the bearing plate 52.

The stoppers 55 include female screw portions that are screwed into the spiral grooves of the adjustment shafts 54, and are incorporated into the insides of the two groove portions 53*x* that are formed in the first guide portion 53*e* of the guide block 53 in a state in which the female screw portions are screwed onto the spiral groove. In this state, the stoppers 55 have movement in the axial direction guided by the wall surface including the guide surface 53*xa*. When the adjustment shaft 54 is rotated, the stopper 55 advances and retracts in the axial direction of the adjustment shaft 54. Further, in the stopper 55, a concave portion 55*a* which the convex portion 41*f* of the connecting member 41 abuts on and engages with is formed.

The screwing member 51 is provided to restrict rotation of the adjustment shafts 54 and position the stoppers 55 in predetermined positions. In the screwing member 51, a section is formed into a substantially L-shape as a whole, and a distal end portion of a short arm portion thereof is folded further inward to form a distal end folded portion 51*b*. The screwing member 51 is formed by folding of a metallic plate member or the like, or cutting or the like of a metal block or the like. The screwing member 51 is fixed to the bearing plate 52 by being screwed thereto by a screw 51*a* as described above. At this time, the distal end folded portion 51*b* of the screwing member 51 engages with the adjusting cross groove 54*aa* of the head portion 54*a* of the adjustment shaft 54, and thereby rotation of the adjustment shaft 54 is restricted. In this case, the adjusting cross groove 54*aa* is fixable to the distal end folded portion 51*b* at each rotation angle of 90 degrees (¼ rotation). Note that on an occasion of positional adjustment of the stopper 55 by the adjustment shaft 54, the rotational angle of about 90 degrees of the adjustment shaft 54 does not have a large effect on adjustment of the bending angle. Further, in FIG. 13 to FIG. 15, illustration of the screwing member 51 is omitted.

Further, as shown in FIG. 14 and FIG. 15, in order to prevent the adjustment shaft 54 in the state in which the adjustment shaft 54 is mounted and assembled to the bending angle adjustment mechanism 50 from falling off, a convex portion 53*y* that protrudes outward in a direction orthogonal to one flat surface of the second guide portion 53*f* is formed at a site to be an insertion port for the adjustment shaft 54, that is, a region facing the through-hole 52*d* of the one end side folded portion 52*c* of the bearing plate 52 when the bearing plate 52 is mounted to the guide block 53, and on the one flat surface of the second guide portion 53*f* (surface at a rear side with respect to a surface where the two groove portions 53*x* are formed). As shown in FIG. 13 to FIG. 15, the convex portion 53*y* is formed by, in a section thereof, having an inclined surface at the distal end side of the guide block 53, that is, at a site near to the second guide portion 53*f*, while a surface that faces the proximal end side of the guide block 53, that is a site near to the first guide portion 53*f*, that is, the head portion 54*a* of the adjustment shaft 54 that is mounted is formed by a wall surface having a flat surface orthogonal to the axial direction of the guide block 53.

Further, a height dimension H of the convex portion 53*y* (see FIG. 14), that is, a protruding amount is set as follows. That is, the protruding amount is set so that the convex portion 53*y* protrudes to be higher than a lower edge position of an outer circumferential edge portion of the head portion 54*a* of the adjustment shaft 54, in a state in which the adjustment shaft 54 is disposed in a normal position in the bending angle adjustment mechanism 50. Here, the normal position of the adjustment shaft 54 refers to a position on an occasion of the adjustment shaft 54 being incorporated in the bending angle adjustment mechanism 50 in a state in which both the ends of the adjustment shaft 54 are rotatably supported by the through-holes 52*d* and 52*e* in both the end folded portions of the bearing plate 52.

As described above, the guide block 53 is formed from a raw material having elasticity. Accordingly, when the present bending angle adjustment mechanism 50 is assembled, the adjustment shaft 54 is inserted through the through-hole 53*d* of the guide block 53 and the through-hole 52*d* of the bearing plate 52, and thereafter, the end portion of the adjustment shaft 54 is rotatably engaged with the through-hole 53*bb* of the guide block 53 and the through-hole 52*e* of the bearing plate 52. Thereby, both the ends of the adjustment shaft 54 are rotatably supported pivotally by the guide block 53 and the bearing plate 52. In this case, in the stage before the adjustment shaft 54 is brought into a state pivotally supported completely in a predetermined position, the outer circumferential edge portion of the head portion 54*a* of the adjustment shaft 54 abuts on the above described convex portion 53*y*, and movement in the insertion direction of the adjustment shaft 54 in the axial direction is inhibited. Here, since the guide block 53 itself has elasticity, if the adjustment shaft 54 is directly pushed into the axial direction, the convex portion of the guide block 53 elastically deforms to allow the head portion 54*a* of the adjustment shaft 54 to pass through. Thereby, the adjustment shaft 54 can be placed in the predetermined normal position (the position shown in FIG. 15). In a state in which the adjustment shaft 54 is in the normal position shown in FIG. 15, and fixation of the adjustment shaft 54 by the screwing member 51 is not performed, the adjustment shaft 54 is in a state movable in the axial direction. However, in the bending angle adjustment mechanism 50 of the present embodiment, the convex portion 53*y* is provided at the guide block 53, and therefore, even if the adjustment shaft 54 moves to the position in which the outer circumferential edge portion of the head portion 54*a* abuts on the convex portion 53*y*, the adjustment shaft 54 does not move any more in the direction in which the adjustment shaft 54 falls off in the axial direction. Accordingly, by the above configuration, the convex portion 53*y* is a site that has a function of preventing falling-off of the adjustment shaft 54, and preventing damage or the like to the spiral groove due to falling-off.

The bending angle adjustment mechanism 50 of the present embodiment configured as above is assembled roughly as follows. First, the bearing plate 52 is mounted to the guide block 53. To this end, the one end side folded portion 52*c* of the bearing plate 52 is caused to abut on the wall surface 53c of the guide block 53, and the other end side folded portion 52b of the bearing plate 52 is fitted into the concave portion 53b of the guide block 53.

In this state, the other end portion of the adjustment shaft 54 is inserted through the through-hole 53d in the wall surface 53c of the guide block 53 via the through-hole 52d of the one end side folded portion 52c of the bearing plate 52. Subsequently, the adjustment shaft 54 is forced in so that the spiral portion of the adjustment shaft 54 is housed inside the groove portion of the guide block 53. At this time, the stopper 55 is screwed onto the spiral portion of the adjustment shaft 54. The stopper 55 is placed in the groove portion of the guide block 53, between the other end side folded portion 52b and the one end side folded portion 52c of the bearing plate 52. Subsequently, the other end portion of the adjustment shaft 54 is engaged with the through-hole 52e of the other end side folded portion 52b of the bearing plate 52 via the through-hole 53bb of the concave portion 53b of the guide block 53.

When the adjustment shaft 54 is inserted, the head portion 54a of the adjustment shaft 54 abuts on the convex portion 53y of the guide block 53, and temporarily inhibits insertion of the adjustment shaft 54 in the axial direction. Here, since the guide block 53 is formed to have elasticity, if the adjustment shaft 54 is directly forced in the axial direction, the head portion 54a bends the placement portion of the convex portion 53y downward while riding over the convex portion 53y along the inclined surface of the convex portion 53y of the guide block 53, and causes the convex portion 53y to retract from the traveling direction of the adjustment shaft 54. Accordingly, the adjustment shaft 54 can be inserted in the axial direction without hindrance. In this manner, the adjustment shaft 54 is pivotally supported rotatably with respect to the bearing plate 52 in the sites in the vicinities of both the end portions. Note that the adjustment shafts 54 are placed in the two groove portions of the guide block 53 one by one. At this time, the two adjustment shafts 54 are disposed parallel in the two groove portions of the guide block 53. In this state, the adjustment shafts 54 are disposed in a state in which a part of the guide block 53 is sandwiched between the adjustment shafts 54 and the bearing plate 52 which supports both the ends of the adjustment shafts 54. Thereby, the present bending angle adjustment mechanism 50 is an integral structure as one unit.

For the configuration unit in which the bearing plate 52, the guide block 53 and the adjustment shaft 54 are integrated as above, if the adjustment shaft 54 is normally and reversely rotated by applying a tool such as a plus driver to the adjusting cross groove 54aa, the stopper 55 moves to advance and retreat in the axial direction while being guided by the guide surface 53xa.

In endoscopes to which the bending angle adjustment mechanisms 50 of the present embodiment are applied, maximum bending angles to be set differ respectively in accordance with use purposes and types of the endoscopes. Therefore, in the bending angle adjustment mechanism 50, the positions of the above described stoppers 55 on the adjustment shafts 54 are set to predetermined positions, and thereby the maximum bending angles in the respective endoscopes are specified.

After the positions of the stoppers 55 on the adjustment shafts 54 are properly set by the above described means, the distal end folded portion 51b of the screwing member 51 is engaged with the adjusting cross groove 54aa of the head portion 54a of the adjustment shaft 54. In this state, the through-hole 51aa of the screwing member 51 and the screw hole 52g of the bearing plate 52 are caused to correspond to each other, and the screw 51a is screwed therein. Thereby, the screwing member 51 is fixed by screw to the bearing plate 52. Thereby, rotation of the adjustment shafts 54 is locked, and therefore, the stoppers 55 are positioned and fixed to the predetermined positions, whereby the set maximum bending angle is specified to be the predetermined value, and is not easily deviated.

Incidentally, in the operation portion in the endoscope 1 to which the bending angle adjustment mechanism 50 of the present embodiment is applied, reduction in thickness of members configuring a rear cylinder is adopted, in order to reduce a weight of the rear cylinder. The rear cylinder in the operation portion is usually provided with a groove-shaped portion for performing rotation position restriction, and if the rear cylinder is reduced in thickness, there arises the problem of being unable to ensure a depth of the groove-shaped portion sufficiently.

Figure 18:
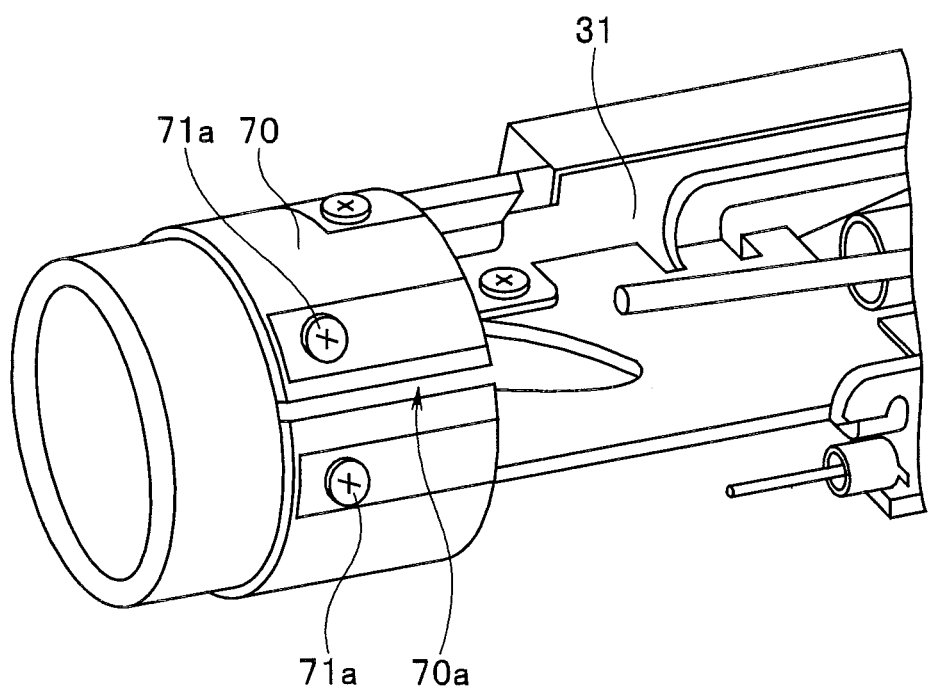
FIG. 18 is an essential part schematic perspective view showing a shape of a rear cylinder in an endoscope to which the bending angle adjustment mechanism of one embodiment of the present invention is applied.

For the above reason, in the present endoscope 1, a rear cylinder 70 of the operation portion is configured by a form as shown in FIG. 18. That is, the rear cylinder 70 of the present endoscope 1 includes a member formed into a substantially cylindrical shape, and a cutout portion 70a is provided at a part thereof. The cutout portion 70a is a groove-shaped portion for performing rotation position restriction for the rear cylinder 70, and is a groove-shaped portion which is cut out by completely penetrating through the rear cylinder 70. In the rear cylinder 70, hole portions for allowing screws 71a for screwing and fixing the rear cylinder 70 to the main frame 31 to be inserted through are formed in sites at both sides facing to each other with the above described cutout portion 70a therebetween. By the configuration, strength of the rear cylinder 70 can be also ensured while the groove portion with a depth of the plate thickness of the rear cylinder 70 or more is ensured.

As described above, according to the above described one embodiment, the convex portion 53y that prevents falling-off of the adjustment shaft 54 is provided at the guide block 53, and therefore, damage or the like to the spiral groove due to falling-off of the adjustment shaft 54 can be prevented. Further, in the state in which the adjustment shafts 54 are placed in the guide block 53, substantially all the regions of the spiral grooves are configured to be protected by contrivance of the shape of the guide block 53, and therefore, the region of the spiral groove provided in the adjustment shaft 54 can be ensured more. At the same time, with respect to the structure which has conventionally performed protection of the spiral grooves by using stoppers, the stoppers 55 themselves can be downsized and the moving amounts of the stoppers 55 in the axial direction on the adjustment shaft 54 can be significantly ensured. Further, the protection shape of the spiral grooves by the guide block 53 is formed to guide the three surfaces of the stoppers 55, and therefore, contributes to performing movement in the axial direction of the stopper 55 smoothly without play.

As a result that downsizing of the stopper 55 is realized, it is not necessary to prepare a stopper in a different shape (length) for each model, and the stopper in the single shape can be adopted. Accordingly, simplification of the mechanism is realized by commonality of the components, and a contribution can be made to reduction in the number of components. With this, a contribution also can be made to simplification of the manufacture process and simplification of component management and product management. Consequently, a contribution can be made to reduction in manufacture cost.

Furthermore, according to the present embodiment, the integrated (unitized) structure of the mechanism is realized, and thereby, the bending angle adjustment mechanism 50 can be mounted to the main frame 31 in the operation portion 3 of the endoscope 1 as one unit only by screwing fixation. Accordingly, simplification of the assembly process at a time of manufacture can be realized. In addition thereto, reduction in the number of components can be realized, and therefore, a contribution can be made to reduction in the manufacture cost.

Incidentally, two of the bending angle adjustment mechanisms 50 of the aforementioned embodiment are placed in the operation portion 3 of the endoscope 1. That is, the bending angle adjustment mechanisms 50 are placed in respective predetermined positions in an upper half part and a lower half part with a line designated by reference sign D in FIG. 2 (a center axis line of the operation portion passing through the center of rotation of the sprocket 33 and along the longitudinal direction of the operation portion 3) as a center, that is, respective positions on the traveling path of the chain 32. Accordingly, the two of the bending angle adjustment mechanisms 50 are disposed in such positions as to be substantially line symmetrical with respect to the above described axial line D in the respective positions. Here, the respective bending angle adjustment mechanisms 50 include totally similar functions, and the bending angle adjustment mechanisms of totally similar configurations are applied. In this case, the shapes of the respective component members configuring the two of the bending angle adjustment mechanisms 50 are formed into symmetrical shapes (see FIG. 3 and FIG. 4). Consequently, in the bending angle adjustment mechanism 50 of the present embodiment, the shapes of the bearing plate 52 and the guide block 53 which are formed into symmetrical shapes among the component members are formed as follows. That is, the guide block 53 is formed to be axially symmetrical with an axial line (an alternate long and short dash line) that extends in the longitudinal direction and shown by reference sign D1 in FIG. 10 as a center. Further, the bearing plate 52 is formed to be axially symmetrical with an axial line (an alternate long and short dash line) that is orthogonal to the axial line D1 and is shown by reference sign D2 in FIG. 10 as a center.

If the configurations as above are adopted, commonality of the component members configuring the two of bending angle adjustment mechanisms 50 can be achieved. Accordingly, a contribution can be made to reduction in the kinds of components, and die cost for molding components can be reduced, and a contribution can be made to reduction in manufacture cost.

Figure 16:
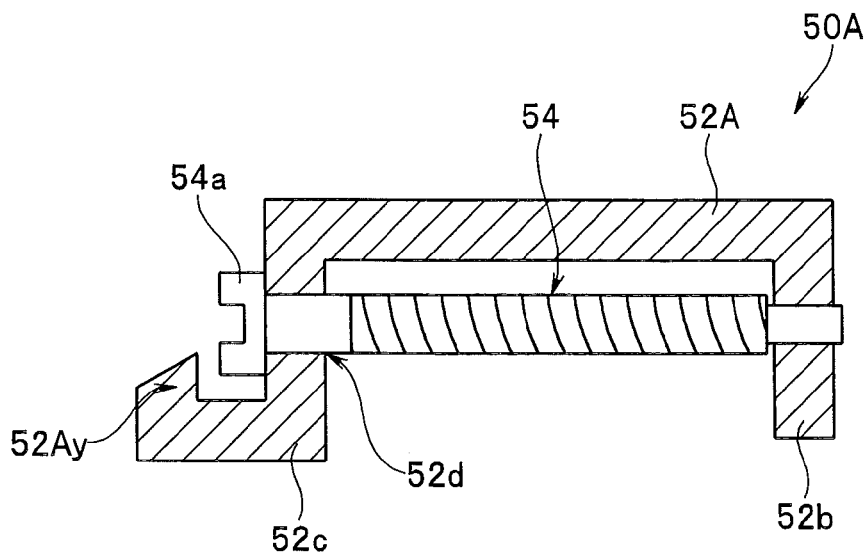
FIG. 16 is an essential part enlarged sectional view showing a first modification of the bending angle adjustment mechanism of one embodiment of the present invention.
Figure 17:
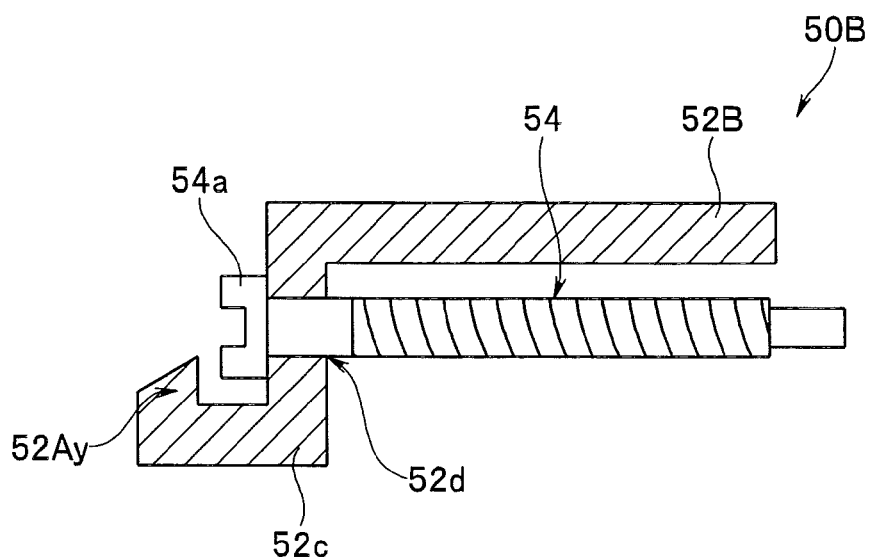
FIG. 17 is an essential part enlarged sectional view showing a second modification of the bending angle adjustment mechanism of one embodiment of the present invention.

In the bending angle adjustment mechanism 50 of the aforementioned one embodiment, the convex portion 53y is configured to be provided at a part of the guide block 53 in order to prevent falling-off of the adjustment shaft 54. The contrivance to prevent falling-off of the adjustment shaft 54 is not limited to the above configuration, and another means is also conceivable. For example, FIG. 16 and FIG. 17 show two modifications of the means for preventing falling-off of the adjustment shaft in the bending angle adjustment mechanism. The two modifications are examples of forming sites which replace the convex portion 53y in the bending angle adjustment mechanism of the above described one embodiment by devising the shape of the bearing plate 52.

FIG. 16 shows a first modification of the bending angle adjustment mechanism of the above described one embodiment, and is an essential part enlarged sectional view showing a part of the mechanism under enlargement. The present modification is substantially similar to the configuration of the aforementioned one embodiment basically, and differs in the shape of the bearing plate in the bending angle adjustment mechanism. With the above, the modification differs in that the convex portion is not formed at the guide block (not illustrated).

In the first modification, a bearing plate 52A is formed into the same shape as the shape of the bearing plate 52 in the aforementioned one embodiment, in the other end side folded portion 52b, the flat surface portion, and the one end side folded portion 52c. In the bearing plate 52A of the present modification, the one end side folded portion 52c is further extended in the axial direction from a distal end of the one end side folded portion 52c, and a most distal end portion thereof is formed into a form folded upward, that is, to a direction orthogonal to the axial direction of the adjustment shaft 54 and to a side where the adjustment shaft 54 is placed. The folded portion is formed as a folded convex portion 52Ay which replaces the convex portion 53y in the above described one embodiment. The folded convex portion 52Ay is formed at a distal end of a cantilever-shaped site with a distal end site of the one end side folded portion 52c as a support shaft. Here, the lever-shaped site that extends in the axial direction from the distal end site of the one end side folded portion 52 is formed by having elasticity. Further a protruding amount of the folded convex portion 52Ay is set to protrude to be higher than the lower edge position of the outer circumferential edge portion of the head portion 54a of the adjustment shaft 54 in a state in which the adjustment shaft 54 is disposed in a normal position in a bending angle adjustment mechanism 50A, similarly to the above described convex portion 53y.

By the above configuration, the head portion 54a presses down and bends the folded convex portion 52Ay when the adjustment shaft 54 is inserted and disposed, whereby the adjustment shaft 54 can be moved in the axial direction without hindrance. Further, in the state in which the adjustment shaft 54 is placed in the predetermined position, the head portion 54a abuts on the folded convex portion 52Ay, and thereby, falling-off of the adjustment shaft 54 is prevented.

FIG. 17 shows a second modification of the bending angle adjustment mechanism of the above described one embodiment, and is an essential part enlarged sectional view showing a part of a mechanism under enlargement. The present modification has a configuration substantially similar to the configuration of the first modification, and differs in a shape of a bearing plate in a bending angle adjustment mechanism.

That is, in the second modification, a bearing plate 52B is formed into a shape in which the other end side folded portion 52b is omitted, with respect to the bearing plate 52A of the first modification. The other components are similar to the components of the first modification.

The bearing plate 52B of the present modification adopts a configuration in which the other end side folded portion 52b is omitted, and the other end of the adjustment shaft 54 is rotatably supported pivotally in a fixing portion not illustrated. Accordingly, a configuration and an operation of the folded convex portion 52Ay in the present modification is similar to the configuration and the operation of the above described first modification. By the configuration as above, an effect totally similar to the effects of the aforementioned one embodiment and the first modification can be obtained.

Incidentally, the bending angle adjustment mechanism of the aforementioned one embodiment is configured to perform position adjustment of the stoppers 55 by providing the female screws in the stoppers 55, screwing the female screws onto the threaded portions of the adjustment shafts 54, and rotating the adjustment shafts 54. In the configuration, adjustment shaft rotation restricting means for restricting rotation of the stoppers 55 that have positions adjusted as described above, and fixing the adjustment shafts 54 in optional adjustment positions is needed. Therefore, the present embodiment adopts the configuration that mounts the screwing member 51 that is the rotation preventing member to the bearing plate 52 by using the screw 51a, as the adjustment shaft rotation restricting means.

In the above case, the respective screwing members 51 include the screwing member 51 for the up direction and the left direction (UL) bending fixation and the screwing member 51 for the down direction and the right direction (DR) bending fixation, and both the screwing members 51 are disposed to be line symmetry with respect to the center axis in the longitudinal direction of the operation portion 3. The respective screwing members 51 are fixed by screw in a form facing the center axis of the above described operation portion 3. For this reason, when the respective screwing members 51 are screwed and fixed to the bearing plates 52, it is necessary to have an access to the operation portion 3 from different directions which are opposite to each other. Therefore, a procedure of passing a jig such as a driver from one hand to another to fix the other after fixing one, or changing an orientation of (the operation portion 3: a working target of) the endoscope 1, or changing a position where a worker faces the operation portion 3 (working target) of the endoscope 1, or the like, and efficiency at the time of an assembly work is not favorable. Further, when the endoscope 1 (working target) during assembly work is moved, contents which are not fixed are likely to move, as a result of which, variation occurs to the state after completion of assembly, and degradation in quality is sometimes caused. For this reason, there is a demand to avoid moving a working target at the time of assembly work as much as possible.

Figure 19:
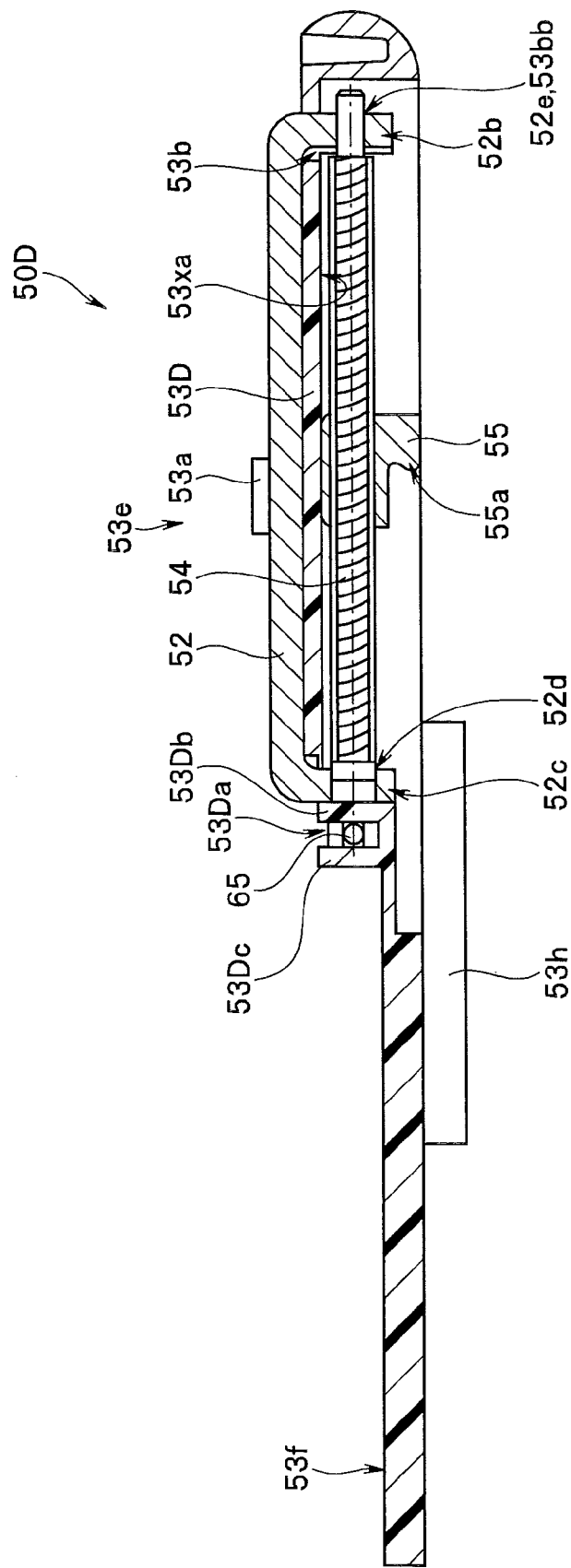
FIG. 19 is a sectional view of a third modification of the bending angle adjustment mechanism of one embodiment of the present invention.
Figure 20:
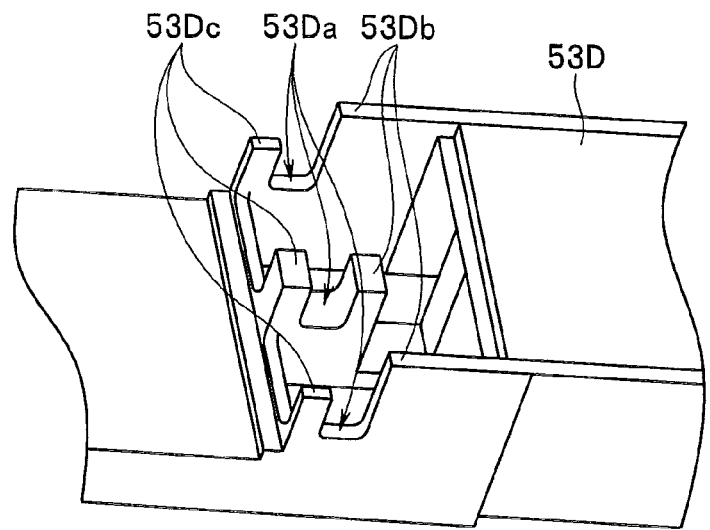
FIG. 20 is an essential part enlarged perspective view showing a part of a guide block out of component members of the bending angle adjustment mechanism of FIG. 19 under enlargement.
Figure 21:
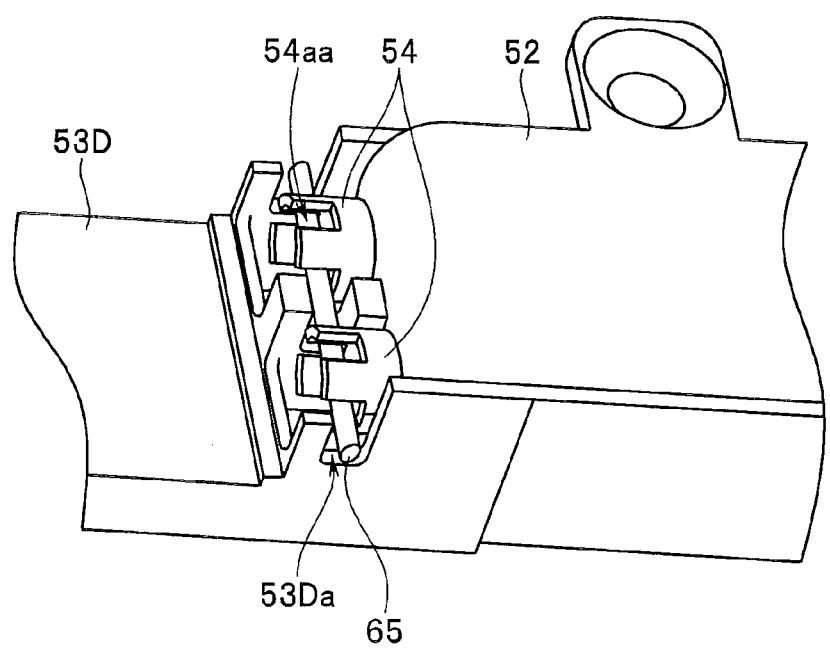
FIG. 21 is an essential part enlarged perspective view showing a state in which a bearing plate and two adjustment shafts are incorporated into a guide plate and are fixed to the guide block of FIG. 20 with a fixing pin.

Consequently, in a third modification that will be described hereinafter, a configuration is devised with assembly work efficiency taken into consideration, and reduction in the number of components is realized, whereby a configuration that contributes to further reduction in manufacture cost is proposed. FIG. 19 to FIG. 21 are views showing the third modification of the bending angle adjustment mechanism of the one embodiment of the present invention. Among the drawings, FIG. 19 shows a sectional view of a bending angle adjustment mechanism of the present modification, and corresponds to FIG. 13 of the above described one embodiment. FIG. 20 is an essential part enlarged perspective view showing a part of a guide block out of component members of the bending angle adjustment mechanism of the present modification. FIG. 21 is an essential part enlarged perspective view showing a state in which a bearing plate and two adjustment shafts are incorporated into a guide plate and are fixed to the guide block of FIG. 20 with a fixing pin.

Note that the third modification which will be described as follows basically includes a configuration substantially similar to the configuration of the aforementioned one embodiment, and only slightly differs in the shape of a guide block 53D in the present modification. Accordingly, component members and component portions similar to the component members and the component portions of the aforementioned one embodiment are assigned with the same reference signs, and detailed explanation thereof will be omitted.

In the present modification, in the guide block 53D, a shape of a site on which the head portion 54a of the adjustment shaft 54 differs. That is, in the guide block 53D, a groove portion 53Da as shown in FIG. 19 is formed in a site on which the head portion 54a of the adjustment shaft 54 which is inserted through and disposed in a through-hole 53d. The groove portion 53Da is formed by a wall surface 53Db that holds a neck portion of the above described head portion 54a, and a wall surface 53Dc that is formed in a position facing the wall surface 53Db to be opposite to each other. Further, the groove portion 53Da is formed to be oriented to a direction that is not parallel to the axial direction of the adjustment shaft 54, for example, a direction substantially orthogonal to the axial direction of the above described adjustment shaft 54, in the guide block 53D. The other components are substantially similar to the components in the above described one embodiment.

By the above configuration, in the guide block 53D of the present modification, the head portion 54a of the adjustment shaft 54 is disposed in the groove portion 53Db that is formed by the two wall surfaces 53Db and 53Dc which are provided to be opposite to each other. Accordingly, when the guide block 53D is seen from a side portion of the above described groove portion 53Db, the groove portions 53Db and the adjusting cross grooves 54aa of the head portions 54a of the two adjustment shafts 54 are sometimes in an overlapping state. A fixing pin 65 is inserted in the above portion. Thereby, the two adjustment shafts 54 are simultaneously restricted from rotating.

Note that as the fixing pin 65, a spring pin is applied, and the spring pin may be configured to be inserted by press-fitting, or a parallel pin may be configured to be inserted. Here, the fixing pin 65 needs to be kept in an inserted state. When a spring pin is applied as the fixing pin 65, the spring pin is inserted while the spring pin is press-fitted, and therefore, the pin after insertion does not fall off. Even if a parallel pin is applied as the fixing pin 65, the inserted parallel pin does not fall off for the following reason.

That is, after position adjustment of the stoppers 55 by the adjustment shafts 54, a parallel pin as the fixing pin 65 is inserted in a portion where the groove portions 53Db of the guide block 53D and the adjusting cross grooves 54aa of the head portions 54a of the two adjustment shafts 54 overlap one another, and a bending angle adjustment mechanism 53D is assembled. The bending angle adjustment mechanism 53D which is thus assembled is placed in a predetermined position in the inside of the operation portion 3 of the endoscope 1. In this case, in an inserting and an extracting direction of the fixing pin 65, the main frame 31 and the exterior member inner face of the operation portion 3 are placed. Therefore, if the bending angle adjustment mechanism 53D is in a state incorporated in the inside of the operation portion 3, the fixing pin 65 is in a state incapable of being inserted and extracted. Therefore, the rotation of the adjustment shafts 54 is always restricted, and thereby the adjustment positions of the stoppers 55 are kept.

By the above configuration, according to the above described third modification, the screwing member 51 and the screw 51a can be omitted out of the component members which are applied in the conventional bending angle adjustment mechanism. Accordingly, the function similar to the conventional bending angle adjustment mechanism can be ensured by a simpler configuration. Reduction in the number of components, and simplification of the assembly process are realized, and thereby a contribution can be made to reduction in manufacture cost.

Note that the present invention is not limited to the aforementioned embodiment, and various modifications and applications can be carried out within the range without departing from the gist of the invention as a matter of course. Further, the above described embodiment includes the inventions at various stages, and by proper combination in the plurality of components that are disclosed, various inventions can be extracted. For example, even when some components are deleted from all the components shown in the above described one embodiment, if the problem to be solved by the invention can be solved, and the effect of the invention is obtained, the configuration from which the components are deleted can be extracted as the invention.

The present invention can be applied not only to the endoscopes in the medical field, but also to the endoscopes in the industrial field.

What is claimed is:

1. A bending angle adjustment mechanism for an endoscope, comprising:
   a rod member that is disposed along a traveling path of a long member that is connected to a bending portion that is bendable and is pulled;
   a support member made of metal that is integrally provided to support both ends of the rod member;
   an adjustment piece that is engaged with the rod member, is movable along the rod member, and restricts movement of the long member; and
   a guide member made of resin having a guide surface for guiding movement of the adjustment piece;
   wherein
   the guide member is fixed in a state in which the guide member is sandwiched between the adjustment piece and the support member so that the guide surface is disposed in a position capable of guiding the adjustment piece.

2. The bending angle adjustment mechanism for an endoscope according to claim 1, wherein in the rod member, a threaded portion is formed on a surface.

3. The bending angle adjustment mechanism for an endoscope according to claim 2, wherein the support member is a plate-shaped member that is provided to be substantially parallel to a longitudinal direction of the rod member, and has both ends formed into plate shapes that are bent at substantially right angles.

4. The bending angle adjustment mechanism for an endoscope according to claim 3, further comprising:
   a rotation preventing member that prevents the rod member from rotating with respect to the guide member, with the longitudinal direction of the rod member as an axis.

5. The bending angle adjustment mechanism for an endoscope according to claim 1, wherein the guide member has a groove portion integrally forming a plurality of the guide surfaces.

6. The bending angle adjustment mechanism for an endoscope according to claim 1, further comprising:
   a snap fit that fixes the guide member to the support member.

7. An endoscope comprising the bending angle adjustment mechanism according to claim 1.

* * * * *